(12) United States Patent
Chang et al.

(10) Patent No.: US 10,113,208 B2
(45) Date of Patent: Oct. 30, 2018

(54) **COMBINATORIAL METABOLIC ENGINEERING OF *SACCHAROMYCES CEREVISIAE* FOR TERMINAL ALKENE PRODUCTION**

(71) Applicant: National University of Singapore, Singapore (SG)

(72) Inventors: Matthew Wook Chang, Singapore (SG); Binbin Chen, Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 15/339,239

(22) Filed: Oct. 31, 2016

(65) Prior Publication Data

US 2017/0121720 A1 May 4, 2017

Related U.S. Application Data

(60) Provisional application No. 62/249,432, filed on Nov. 2, 2015.

(51) Int. Cl.
| | |
|---|---|
| *C12N 15/81* | (2006.01) |
| *C10L 1/04* | (2006.01) |
| *C12P 5/02* | (2006.01) |
| *C12N 9/88* | (2006.01) |
| *C12N 9/00* | (2006.01) |
| *C12N 9/08* | (2006.01) |
| *C10G 3/00* | (2006.01) |

(52) U.S. Cl.
CPC ........ *C12Y 401/01072* (2013.01); *C10G 3/00* (2013.01); *C12N 9/0065* (2013.01); *C12N 9/88* (2013.01); *C12N 9/93* (2013.01); *C12P 5/026* (2013.01); *C12Y 111/01005* (2013.01); *C12Y 111/01006* (2013.01); *C12Y 403/01* (2013.01); *C12Y 602/01003* (2013.01); *C10G 2400/22* (2013.01); *C10L 2290/26* (2013.01)

(58) Field of Classification Search
None
See application file for complete search history.

(56) References Cited

U.S. PATENT DOCUMENTS

| | | |
|---|---|---|
| 2010/0330642 A1 | 12/2010 | Ridley et al. |
| 2013/0130344 A1 | 5/2013 | Lee et al. |
| 2014/0186877 A1 | 7/2014 | Reppas et al. |

FOREIGN PATENT DOCUMENTS

WO WO 2014/102201 A1 7/2014

OTHER PUBLICATIONS

Belcher, J., et al., "Structure and Biochemical Properties of the Alkene Producing Cytochrome P450 OleTJE (CYP152L1) from the *Jeotgalicoccus* sp. 8456 Bacterium," *Journal of Biological Chemistry*, vol. 289, pp. 6535-6550, Mar. 7, 2014.

Beller, H. R., et al., "Genes Involved in Long-Chain Alkene Biosynthesis in *Micrococcus luteus*," *Applied and Environmental Microbiology*, vol. 76, pp. 1212-1223, Feb. 15, 2010.

Black, P. N., et al., "Yeast acyl-CoA synthetases at the crossroads of fatty acid metabolism and regulation," *Biochimica et Biophysica Acta (BBA)—Molecular and Cell Biology of Lipids*, vol. 1771, pp. 286-298, 2007.

Chen, B., et al., "Combinatorial metabolic engineering of *Saccharomyces cerevisiae* for terminal alkene production", *Metabolic Engineering*, 31: 53-61 (2015).

Cho, J.-Y., et al., "Transcriptional Control of ADH Genes in the Xylose-Fermenting Yeast *Pichia stipitis*," *Applied and Environmental Microbiology*, vol. 65, pp. 2363-2368, Jun. 1, 1999.

Conrado, R. J., "DNA-guided assembly of biosynthetic pathways promotes improved catalytic efficiency," *Nucleic Acids Research*, vol. 40, pp. 1879-1889, Feb. 1, 2012.

Davis, M. D., et al., "Inhibition of *Escherichia coli* Acetyl Coenzyme A Carboxylase by Acyl-Acyl Carrier Protein," *Journal of Bacteriology*, vol. 183, pp. 1499-1503, Feb. 15, 2001.

de Jong, B., et al., "Systems biology of yeast: enabling technology for development of cell factories for production of advanced biofuels," *Current opinion in biotechnology*, Dec. 12, 2011.

Gibson, D. G. , et al., "Enzymatic assembly of DNA molecules up to several hundred kilobases," *Nat Meth*, vol. 6, pp. 343-345, 2009.

Güldener, U., et al., "A New Efficient Gene Disruption Cassette for Repeated Use in Budding Yeast," *Nucleic Acids Research*, vol. 24, pp. 2519-2524, Jul. 1, 1996.

Hahn-Hagerdal, B., et al., "Role of cultivation media in the development of yeast strains for large scale industrial use," *Microbial cell factories*, vol. 4, p. 31, 2005.

Howard, T. P., et al. "Synthesis of customized petroleum-replica fuel molecules by targeted modification of free fatty acid pools in *Escherichia coli*," Proceedings of the *National Academy of Sciences*, Apr. 22, 2013.

Izawa, S., et al., "Importance of catalase in the adaptive response to hydrogen peroxide: analysis of acatalasaemic *Saccharomyces cerevisiae*," *Biochem. J.*, vol. 320, pp. 61-67, Nov. 15, 1996.

Kalscheuer, R., et al., "Synthesis of Novel Lipids in *Saccharomyces cerevisiae* by Heterologous Expression of an Unspecific Bacterial Acyltransferase," *Applied and Environmental Microbiology*, vol. 70, pp. 7119-7125, 2004.

(Continued)

Primary Examiner — Channing S Mahatan
(74) Attorney, Agent, or Firm — Hamilton, Brook, Smith & Reynolds P.C.

(57) ABSTRACT

Modified *Saccharomyces cerevisiae* yeast that produce terminal alkenes are described. The modification of the *Saccharomyces cerevisiae* yeast includes insertion of at least one heterologous fatty acid decarboxylase gene, deletion of FAA1 and FAA4, overexpression of HEM3, and triple-deletion of CTT1, CTA1 and CCP1. Methods of producing terminal alkenes by culturing and fermenting the modified *Saccharomyces cerevisiae* yeast and optionally harvesting the terminal alkenes are also described. Mixtures of terminal alkenes produced by the modified *Saccharomyces cerevisiae* yeast, and methods of metabolically engineering a yeast for optimizing overexpression of one or more alkenes are also described.

10 Claims, 6 Drawing Sheets
Specification includes a Sequence Listing.

(56) References Cited

OTHER PUBLICATIONS

Karim, A. S., et al., "Characterization of plasmid burden and copy number in *Saccharomyces cerevisiae* for optimization of metabolic engineering applications," *FEMS yeast research*, vol. 13, pp. 107-116, 2013.
Kizer, L., et al., "Application of Functional Genomics to Pathway Optimization for Increased Isoprenoid Production," *Applied and Environmental Microbiology*, vol. 74, pp. 3229-3241, May 15, 2008.
Leber, C., et al., "Engineering of *Saccharomyces cerevisiae* for the synthesis of short chain fatty acids," *Biotechnology and bioengineering*, 111: (2): 347-358 (2013).
Liu, Y., et al., "Hydrogen peroxide-independent production of α-alkenes by OleTJE P450 fatty acid decarboxylase", *Biotechnology for Biofuels*, 7(1): 28, 12 pgs. (2014).
Lopez de Felipe, F., et al., "Cofactor Engineering: a Novel Approach to Metabolic Engineering in Lactococcus lactis by Controlled Expression of NADH Oxidase," *Journal of Bacteriology*, vol. 180, pp. 3804-3808, Aug. 1, 1998.
Mendez-Perez, D., "Modular Synthase-Encoding Gene Involved in α-Olefin Biosynthesis in *Synechococcus* sp. Strain PCC 7002," *Applied and Environmental Microbiology*, vol. 77, pp. 4264-4267, Jun. 15, 2011.
Mesquita, A., et al., "Caloric restriction or catalase inactivation extends yeast chronological lifespan by inducing H2O2 and superoxide dismutase activity," *Proceedings of the National Academy of Sciences*, vol. 107, pp. 15123-15128, Aug. 24, 2010.
Nevoigt, E., "Progress in Metabolic Engineering of *Saccharomyces cerevisiae*," *Microbiology and Molecular Biology Reviews*, vol. 72, pp. 379-412, Sep. 1, 2008.
Ogiwara, H., et al., "Inhibition of Rat-Liver Acetyl-Coenzyme-A Carboxylase by Palmitoyl-Coenzyme A," *European Journal of Biochemistry*, vol. 89, pp. 33-41, 1978.
Ostergaard, S., et al., "Metabolic Engineering of *Saccharomyces cerevisiae*," *Microbiology and Molecular Biology Reviews*, vol. 64, pp. 34-50, Mar. 1, 2000.
Peralta-Yahya, P. P., et al., "Microbial engineering for the production of advanced biofuels," *Nature*, vol. 488, pp. 320-328 (2012).
Pitera, D. J., et al., "Balancing a heterologous mevalonate pathway for improved isoprenoid production in *Escherichia coli*," *Metabolic Engineering*, vol. 9, pp. 193-207 (2007).
Poirier, M. A., et al., "Selective separation and identification of olefins in petroleum and synthetic fuel naphtha," *Fuel*, vol. 61, pp. 182-184 (1982).
Rude, M.A., et al., "Terminal Olefin (1-Alkene) Biosynthesis by a Novel P450 Fatty Acid Decarboxylase from *Jeotgalicoccus* Species," *Applied and Environmental Microbiology*, vol. 77, pp. 1718-1727, Mar. 1, 2011.
Ruenwai, R., et al., "Overexpression of Acetyl-CoA Carboxylase Gene of Mucor rouxii Enhanced Fatty Acid Content in Hansenula polymorpha," *Molecular Biotechnology*, vol. 42, pp. 327-332 (2009).
Runguphana, W., et al., "Metabolic engineering of *Saccharomyces cerevisiae* for production of fatty acid-derived biofuels and chemicals", *Metabolic Engineering*, 21: 103-113 (2014).
Sadowski, I., et al., "Disintegrator vectors for single-copy yeast chromosomal integration," *Yeast*, vol. 24, pp. 447-455, 2007.
Scalcinati, G., et al., "Combined metabolic engineering of precursor and co-factor supply to increase alpha-santalene production by *Saccharomyces cerevisiae*," *Microbial cell factories*, vol. 11, p. 117, 2012.
Shin, G.-H. , et al., "Overexpression of genes of the fatty acid biosynthetic pathway leads to accumulation of sterols in *Saccharomyces cerevisiae*," *Yeast*, vol. 29, pp. 371-383, 2012.
Stephanopoulos, G., "Synthetic Biology and Metabolic Engineering," *ACS Synthetic Biology*, vol. 1, pp. 514-525, Nov. 16, 2012.
Sukovich, D. J., et al., "Structure, Function, and Insights into the Biosynthesis of a Head-to-Head Hydrocarbon in Shewanella oneidensis Strain MR-1," *Applied and Environmental Microbiology*, vol. 76, pp. 3842-3849, Jun. 15, 2010.
Sukovich, D. J., et al., "Widespread Head-to-Head Hydrocarbon Biosynthesis in Bacteria and Role of OleA," *Applied and Environmental Microbiology*, vol. 76, pp. 3850-3862, Jun. 15, 2010.
Tai, M., et al., "Engineering the push and pull of lipid biosynthesis in oleaginous yeast Yarrowia lipolytica for biofuel production," *Metabolic Engineering*, vol. 15, pp. 1-9 (2013).
Tang, X., et al., "Engineering the fatty acid metabolic pathway in *Saccharomyces cerevisiae* for advanced biofuel production", *Metabolic Engineering Communications*, 2: 58-66 (2015).
Tehlivets, O., et al., "Fatty acid synthesis and elongation in yeast," Biochimica et Biophysica Acta (BBA)—Molecular and Cell Biology of Lipids, vol. 1771, pp. 255-270, 2007.
Verduyn, C., et al., "Hydrogen Peroxide Metabolism in Yeasts," *Applied and Environmental Microbiology*, vol. 54, pp. 2086-2090, Aug. 1, 1988.
Villarreal, D. M., et al., "Enhancement of Recombinant Hemoglobin Production in *Escherichia coli* BL21(DE3) Containing the Plesiomonas shigelloides Heme Transport System," *Applied and Environmental Microbiology*, vol. 74, pp. 5854-5856, Sep. 15, 2008.
Wang, D., et al., "A highly selective route to linear alpha olefins from biomass-derived lactones and unsaturated acids," *Chemical Communications*, vol. 49, pp. 7040-7042, 2013.
Wang, Z., et al., "Production of pyruvate in *Saccharomyces cerevisiae* through adaptive evolution and rational cofactor metabolic engineering," *Biochemical Engineering Journal*, vol. 67, pp. 126-131, 2012.
Welch, J. W., et al., "Very Long-Chain Fatty Acids in Yeast," *Journal of Bacteriology*, vol. 115, pp. 464-466, Jul. 1, 1973.
Yu, K. O., et al., "Engineering of glycerol utilization pathway for ethanol production by *Saccharomyces cerevisiae*," *Bioresource Technology*, vol. 101, pp. 4157-4161, 2010.
Zhang, F., et al., "Metabolic engineering of microbial pathways for advanced biofuels production," *Current opinion in biotechnology*, vol. 22, pp. 775-783, 2011.
Zhang, M., et al., "Hydrogen peroxide production using chemically treated Pichia pastoris cells," *Enzyme and Microbial Technology*, vol. 16, pp. 10-17, 1994.
Zhou, YJ, et al., "Fatty acid-derived biofuels and chemicals production in *Saccharomyces cerevisiae*", *Frontiers in Bioengineering and Biotechnology*, 2(32): 1-6 (2014).

COMBINATORIAL METABOLIC ENGINEERING OF *SACCHAROMYCES CEREVISIAE* FOR TERMINAL ALKENE PRODUCTION

RELATED APPLICATION

This application claims the benefit of U.S. Provisional Application No. 62/249,432, filed on Nov. 2, 2015. The entire teachings of the above application(s) are incorporated herein by reference.

INCORPORATION BY REFERENCE OF MATERIAL IN ASCII TEXT FILE

This application incorporates by reference the Sequence Listing contained in the following ASCII text file being submitted concurrently herewith:
 a) File name: 44591132001.SEQUENCELISTING.txt; created Oct. 28, 2016, 19 KB in size.

BACKGROUND OF THE INVENTION

Global focus towards reducing petroleum footprint has led to a significant interest in developing alternative methods to produce fuels from low-cost and renewable resources. Metabolic engineering has emerged as an enabling technology to this end, which directs modulation of metabolic pathways by using recombinant technologies to overproduce valuable products, including biofuels [4-7]. Alkenes, traditionally used as detergents, lubricating fluids and sanitizers [8], have the potential to serve as "drop-in" compatible hydrocarbon fuels because of their high energy content. In addition, as they are already predominant components of petroleum-based fuels [9, 10], they are compatible with the existing engine platform and fuel distribution systems. Therefore, there is a strong economic and environmental demand for the development of bio-alkenes, which could be low-cost and environmentally sustainable, through metabolic engineering strategies.

The fatty acid biosynthesis pathway is ideally suited to provide biofuel precursors because of the high energy content in the precursors, and these fatty acid precursors can be converted into alkenes via naturally occurring metabolic pathways [1, 11-14]. The first pathway involves a cytochrome P450 fatty acid decarboxylase—OleT$_{JE}$ from *Jeotgalicoccus* sp. ATCC 8456 which directly decarboxylates free fatty acids to terminal alkenes [1-3]. The second pathway employs a multi-domain polyketide synthase, found in the cyanobacterium *Synechococcus* sp. PCC 7002. This enzyme converts fatty acyl-ACP to terminal alkene via an elongation decarboxylation mechanism [11]. The third pathway produces long-chain internal alkenes (C24-C31) by a head-to-head condensation of two acyl-CoA (or-ACP) thioesters followed by several reduction steps in *Micrococcus luteus* [12] and *Shewanella oneidensis* [13, 14]. Among these three pathways, the one-step fatty acid decarboxylation pathway is highly advantageous for alkene biosynthesis for the following two reasons. Firstly, the fatty acid synthesis pathway is feedback-inhibited by fatty acyl-CoA/ACP [15, 16], a precursor of fatty acid-derived biofuels. This feedback inhibition could negatively affect the boosting of fatty acyl-CoA/ACP levels, and in turn the fatty acid-derived biofuel titers. Thus, using free fatty acids as biofuel precursors is more desirable compared with fatty acyl-CoA/ACP. Secondly, a one-step reaction from fatty acids to alkenes reduces intermediate metabolite losses and toxicity [17-19].

The well-studied industrial microorganism *Saccharomyces cerevisiae* offers a number of advantages [20-23] for producing fatty acid-derived products due to i) its ability to withstand lower temperatures, ii) immunity towards phage contaminations, iii) suitability in large-scale fermentation, iv) generally higher tolerance toward abiotic stresses, and v) extensive knowledge available about its fatty acid metabolism.

SUMMARY OF THE INVENTION

Modified *Saccharomyces cerevisiae* yeast that produces terminal alkenes are described. The terminal alkenes include C11-C19 terminal alkenes, for instance 1-undecene, 1-tridecene, 1-pentadecene, 1-heptadecene and 1-nonadecene. The modification of the *Saccharomyces cerevisiae* yeast includes insertion of at least one heterologous fatty acid decarboxylase gene, deletion of FAA1 and FAA4, overexpression of HEM3, and triple-deletion of CTT1, CTA1 and CCP1. The invention also relates to a method of producing terminal alkenes by culturing and fermenting the modified *Saccharomyces cerevisiae* yeast and optionally harvesting the terminal alkenes. The invention further relates to a mixture of terminal alkenes produced by the modified *Saccharomyces cerevisiae* yeast, and a method of metabolically engineering a yeast for optimizing overexpression of one or more alkenes.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

(FIG. 1A) Schematic view of the metabolic pathway for the production of terminal alkenes in the genetically engineered strain. Solid-thin arrows represent the native pathway in *S. cerevisiae*; Solid-thick arrows represent the overexpression of genes in this study; Crosses represent the gene deletion performed. Dashed arrows represent cofactor transfer for OleT utilization. (Abbreviations—ACC1: acetyl-CoA carboxylase; FAS1/2: fatty acid synthase; FAA1/4: fatty acyl-CoA synthetase; PDX1: fatty acyl-CoA oxidase; FOX2: 3-hydroxyacyl-CoA dehydrogenase and enoyl-CoA hydratase; POT1: 3-ketoacyl-CoA thiolase; CCP1: cytochrome c peroxidase; CTA1: catalase A; CTT1: catalase T; HEM1: 5-aminolevulinate synthase; HEM2: aminolevulinate dehydratase; HEM3: porphobilinogen deaminase; HEM4: uroporphyrinogen III synthase; HEM12: uroporphyrinogen decarboxylase; HEM13: coproporphyrinogen oxidase; HEM14: protoporphyrinogen oxidase; HEM15: ferrochelatase; OleT: fatty acid decarboxylase) (FIG. 1B) Synthesis of terminal alkene via fatty acid decarboxylase-OleT catalyzed reaction.

(FIG. 3A) Total alkene titers of the strains without (BY10) and with the engineered fatty acid synthesis pathway (BY11, BY12, BY13 and BY14) are shown in bars. White bar and grey horizontal dash line indicates the alkene titers of the control strain BY10. Alkene fold changes are shown in lines. For alkene fold changes, BY10 was set equal to 1.0 and all values were determined relative to BY10. "+" and "−" indicate with and without engineering respectively. (FIG. 3B) Gas chromatography (GC) profile of the alkene products obtained by batch culture of BY14 (upper trace) and BY10 (lower trace). Filled peaks indicated by arrows were shown as specific alkenes. (FIG. 3C) The comparison of total alkenes produced by the expression of oleT$_{JE}$ homologs in wild-type BY4741 (white bar) and BY4741 Δfaa1Δfaa4 double-deletion strain (grey bar). Alkenes were detected and quantified by GC-MS after growing for 48 h. Results represent the mean of three biological replicates; standard deviations are presented.

(FIG. 6A) Production of alkenes and cell optical density in 1-L fed-batch fermentation using the engineered strain BY22. Samples were withdrawn and analyzed at the indicated time intervals. Diamond-marked line indicates alkene titers and triangle-marked line indicates cell OD. All of the fermentation experiments were performed in triplicate. (FIG. 6B) Titer and fold change summary for alkene production in S. cerevisiae.

DETAILED DESCRIPTION OF THE INVENTION

Figure 1A:
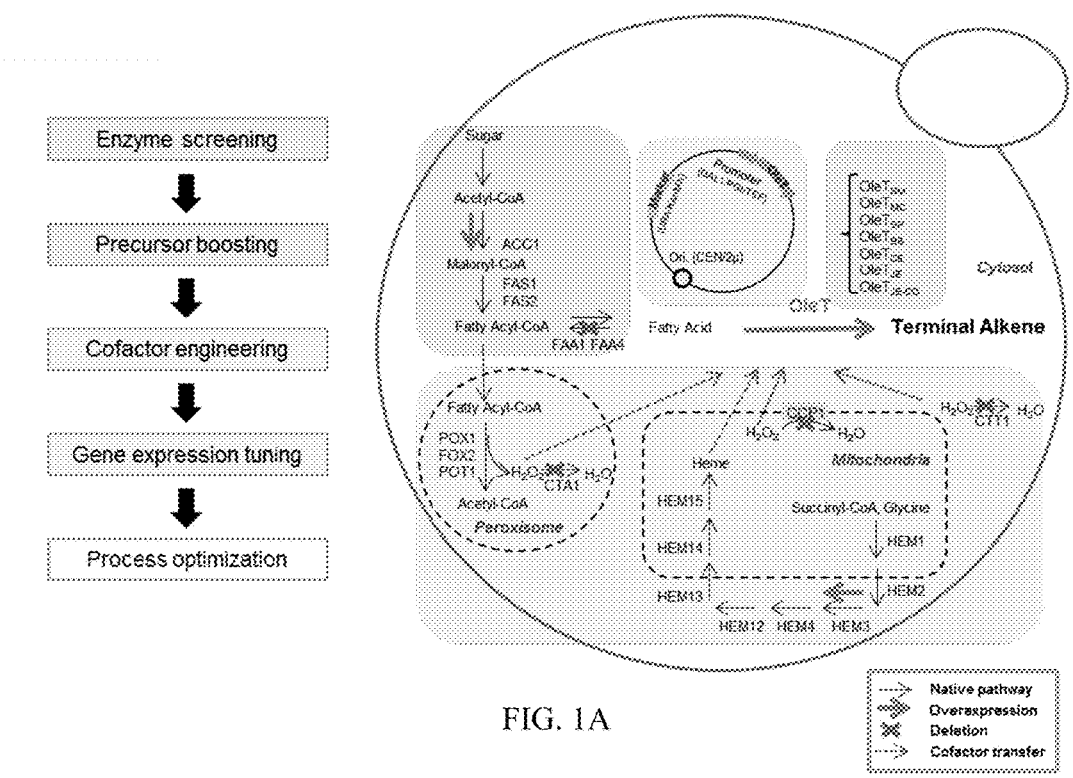
FIGS. 1A-1B.

A description of example embodiments of the invention follows.

The invention pertains, in one aspect, to modified Saccharomyces cerevisiae yeast wherein the modification comprises: insertion of at least one heterologous fatty acid decarboxylase gene, deletion of FAA1 and FAA4, overexpression of HEM3, and triple-deletion of CTT1, CTA1 and CCP1. The modified Saccharomyces cerevisiae yeast can produce at least one terminal alkene, for example, the terminal alkene is 1-undecene, 1-tridecene, 1-pentadecene, 1-heptadecene or 1-nonadecene.

In one aspect, the at least one terminal alkene is produced via a one-step fatty acid decarboxylation pathway. For instance, the decarboxylation is catalyzed by at least one fatty acid decarboxylase. Example fatty acid decarboxylases include OleT$_{SM}$ (SEQ ID NO 1), OleT$_{MC}$ (SEQ ID NO 2), OleT$_{SP}$ (SEQ ID NO 3), OleT$_{BS}$ (SEQ ID NO 4), OleT$_{MP}$ (SEQ ID NO 5), OleT$_{CE}$ (SEQ ID NO 6), OleT$_{JE}$ (SEQ ID NO 7) or OleT$_{JE-CO}$ (SEQ ID NO 8).

In one embodiment, a modified Saccharomyces cerevisiae yeast is characterized by BY22 (BY4741, Δfaa1 Δfaa4 Δctt1 Δcta1 Δccp1, P$_{TEF1}$-HEM3 with pRS41K-P$_{TEF1}$-OleT$_{JE-CO}$).

In another aspect, the invention pertains to a mixture of terminal alkenes comprising at least two terminal alkenes produced by the modified Saccharomyces cerevisiae yeast described herein. The amount of terminal alkenes in the mixture produced by the modified Saccharomyces cerevisiae yeast represents at least a 7-fold increase, at least a 38-fold increase or at least a 67-fold increase, as compared to an amount of terminal alkenes produced by a non-modified Saccharomyces cerevisiae yeast. The mixture of at least two terminal alkenes can be are selected from 1-undecene, 1-tridecene, 1-pentadecene, 1-heptadecene or 1-nonadecene. In some versions the mixture of terminal alkenes comprises at least three terminal alkenes or at least five terminal alkenes, selected from 1-undecene, 1-tridecene, 1-pentadecene, 1-heptadecene or 1-nonadecene.

Methods of producing at least one terminal alkene are also described. In one aspect, the method comprising: culturing the modified Saccharomyces cerevisiae yeast of claim 1 in a rich growth medium; fermenting the culture of modified Saccharomyces cerevisiae yeast at a temperature of about 25° C. to about 35° C. under aerobic conditions to produce at least one terminal alkene, wherein the terminal alkene is 1-undecene, 1-tridecene, 1-pentadecene, 1-heptadecene or 1-nonadecene; and optionally, harvesting the terminal alkene, wherein the harvesting comprises lysing the yeast cells and extracting the terminal alkene.

The rich growth medium can be selected from SC-U+GAL, YPG+G418, YPD+G418 or YPD.

The method of fermenting can be performed with a dissolved oxygen concentration of about 60%. The fermenting can be performed at a temperature of about 30° C. The fermenting can be performed without pH control.

The invention also pertains to methods of metabolically engineering a yeast for optimizing overexpression of one or more alkenes. The method comprises selecting a yeast having inserted therein one or more heterologous decarboxylase genes for alkene biosynthesis in the yeast via free fatty acid decarboxylation; enhancing the metabolic flux towards free fatty acid production in the yeast by disrupting the fatty acid metabolic pathway by deleting at least one synthetase and optionally overexpressing at least one carboxylase; supplying at least one decarboxylase cofactor to the alkene biosynthesis pathway to enhance the metabolic flux towards alkene production in the yeast; tuning expression levels of the one or more heterologous decarboxylase genes by at least one of promoter strength tuning, plasmid copy number tuning and growth medium tuning; and optimizing yeast fermentation conditions by at least one of temperature control, dissolved oxygen concentration control and pH control.

In one version, the supplying of the at least one decarboxylase cofactor is performed internally by the yeast and is performed by at least one of overexpression of one or more rate-limiting enzymes responsible for cofactor biosynthesis and deletion of one or more utilization enzymes that utilize cofactor.

The overexpression of the one or more alkenes by the metabolically engineered yeast can be optimized as compared to a non-engineered yeast.

In light of the foregoing, the inventors aimed to engineer the yeast *S. cerevisiae* to produce terminal alkenes via a one-step fatty acid decarboxylation pathway and to improve the alkene production using combinatorial engineering strategies (see FIG. 1A). First, the inventors screened and characterized eight fatty acid decarboxylases (OleT) to enable and enhance alkene production in *S. cerevisiae*. Then they developed a fatty acid-overproducing strain to boost the precursor availability, which could enhance the metabolic flux (Scalcinati et al., 2012) and resulted in a higher production titer. The inventors then improved the enzyme cofactor accumulation through cofactor genetic engineering [24, 25]. Then they enhanced the cell growth in rich medium and tuned the enzyme expression by optimizing the combinations of the promoters and plasmids. Finally, they further increased the alkene production by optimizing the culturing conditions in bioreactors. This represents the first report of terminal alkene biosynthesis in the yeast *S. cerevisiae*, and the abovementioned combinatorial engineering approaches collectively increased the titer of the alkene production of *S. cerevisiae* 67.4-fold.

Materials and Methods

Strains and Media

*Escherichia coli* TOP10 (Invitrogen) and Luria-Bertani (BD) were used for cloning experiments unless otherwise stated. 100 mg/L ampicillin was used for selection of positive colonies if applicable. *Jeotgalicoccus* sp. ATCC 8456 (NCIMB) was used for oleT$_{JE}$ cloning. The yeast strain *S. cerevisiae* BY4741 (ATCC) was used for functional characterization of OleT enzymes.

*S. cerevisiae* BY4741 wild-type and mutant strains were cultured in rich medium (YPD/YPG), synthetic minimal medium lacking uracil (SC-U), lysine (SC-L), adenine (SC-A), or synthetic minimal induction medium (SC-U-G). YPD/YPG medium (1% yeast extract, 2% peptone and 2% D-glucose/galactose) was used to routinely maintain wild-type strain or cells with pRS41K or pRS42K plasmids. SC-U medium (0.67% yeast nitrogen base, 0.192% uracil dropout and 2% raffinose) was used for growing pESC-URA transformants. SC-L medium (0.67% yeast nitrogen base, 0.18% lysine dropout and 2% glucose) and SC-A medium (0.67% yeast nitrogen base, 0.078% adenine dropout and 2% glucose) was used for selecting positive integrants. SC-U-G medium (0.67% yeast nitrogen base, 0.192% uracil dropout, 1% raffinose and 2% galactose) was used for protein induction in pESC-URA transformants. 2% agar was supplemented for solid media. One mg/mL 5-Fluoroorotic acid (5-FOA, Fermentas) or 200 mg/L geneticin (G418, PAA Laboratories) was used for selection. Heme (20 ug/mL) [26, 27], hydrogen peroxide (0.4 mM every 12 h) [28], or both were supplemented into growth culture where necessary. Yeast growth media components were purchased from Sigma-Aldrich and MP Biomedicals. Yeast cells were cultivated at 30° C. in flasks and shaken at 250 rpm.

Gene Deletion and Integration

Genes were deleted by using the previously described gene disruption cassette containing loxP-kanMX-loxP module in *S. cerevisiae* [29]. Firstly, the gene disruption cassettes were constructed through fusing short homologous sequences with loxP-kanMX-loxP module from plasmid pUG6 (Euroscarf) via a PCR reaction. Following yeast transformation, colonies were selected on an YPD plate containing 200 mg/L G418. The kanMX marker was removed by inducing expression of Cre recombinase from plasmid pSH47 (Euroscarf), which enables subsequent rounds of gene deletion. Here, the correct gene deletion mutants were verified by PCR analysis and used for further gene deletion.

Chromosomal integration was conducted based on the method previously reported by Sadowski et al. [30]. Briefly, genes were firstly cloned into plasmid pIS385 or pIS112 (Euroscarf) containing URA3 selectable marker. The recombinant plasmid was linearized and transformed into *S. cerevisiae*, followed by colony selection performed on SC-U medium. After non-selective growth on YPD plate, individual colonies were replica-plated onto 5-FOA and SC-L or SC-A plates to screen for positive colonies. Finally, the correct integrant was verified by PCR analysis. Oligonucleotide primers used for gene deletion and chromosomal integration are listed in Table 1.

TABLE 1

Primers used in this study. Restriction sites are bold.

| Primers NO. | Primer sequences (5'-3') | SEQUENCE ID. NO. |
|---|---|---|
| OleT$_{JE}$-F | ACGCGGATCCTAAAAAATGTCTACACTTAAGAGGGAT AAGGGCTTAG | SEQ ID NO 9 |
| OleT$_{JE}$-R | ATAAGAATGCGGCCGCCTAATGGTGATGGTGATGATG TGTTCTGTCTACAACTTCGCGAAC | SEQ ID NO 10 |
| ACC1-SC-R | AGAATTTTTGAAAATTCGAATTCAACCCTCACTAAAGG GCGGCCGCACTAGTTAAAAAATGTCTGAAGAAAGCTT ATTCGAGTCTTCTCC | SEQ ID NO 11 |
| ACC1-SC-R | TAAGAGCTCAGATCTTATCGTCGTCATCCTTGTAATCCA TCGATACTAGTCTAATGGTGATGGTGATGATGTTTCAA AGTCTTCAACAATTTTC | SEQ ID NO 12 |
| F AA1-deletion-F | CAATAAAAACTAGAACAAACACAAAAGACAAAAAAAG ACAACAATCAGCTGAAGCTTCGTACGC | SEQ ID NO 13 |
| F AA1-deletion-R | TGCTTTAGTATGATGAGGCTTTCCTATCATGGAAATGTT GATCCAGCATAGGCCACTAGTGGATCTG | SEQ ID NO 14 |
| F AA4-deletion-F | TCTGTTCTTCACTATTTCTTGAAAAACTAAGAAGTACGC ATCAAACAGCTGAAGCTTCGTACGC | SEQ ID NO 15 |

TABLE 1-continued

Primers used in this study. Restriction sites are bold.

| Primers NO. | Primer sequences (5'-3') | SEQUENCE ID. NO. |
|---|---|---|
| F AA4-deletion-R | GTGTTTATGAAGGGCAGGGGGGAAAGTAAAAAACTATGTCTTCCTGCATAGGCCACTAGTGGATCTG | SEQ ID NO 16 |
| pTEF1-F | TTGAGAGCTCTTTCATAGCTTCAAAATGTTTCTACTCCTTTT | SEQ ID NO 17 |
| pTEF1-R | TCAGGGCCCATTTTGTAATTAAAACTTAGATTAGATTGCTATGCTTTC | SEQ ID NO 18 |
| Hem3-F | CTAATCTAAGTTTTAATTACAAAATGGGCCCTGAAACTCTACATATTG | SEQ ID NO 19 |
| HEM3-R | CTTATTTAGTCAATGGTGATGGTGATGATGTTTGATTCTGTCTAAATTAATTTCATCCAG | SEQ ID NO 20 |
| TADH1-F | CATCATCACCATCACCATTGACTAAATAAGCGAATTTCTTATGATTTATGATTTTT | SEQ ID NO 21 |
| TADH1-R | ACGGGGTACCTTTCAGCTGAATTGGAGCGACC | SEQ ID NO 22 |
| CTT 1-deletion-F | TTCTCTTGTCTCATGCCAATAAGATCAATCAGCTCAGCTTCACAACAGCTGAAGCTTCGTACGC | SEQ ID NO 23 |
| CTT 1-deletion-R | TTATGGAGATATAATTACGAATAATTATGAATAAATAGTGCTCTCCGCATAGGCCACTAGTGGATCTG | SEQ ID NO 24 |
| CTA 1-deletion-F | AAATAAATATAATAGTACTTACAAATAAATTTGGAACCCTAGAAGCAGCTGAAGCTTCGTACGC | SEQ ID NO 25 |
| CTA 1-deletion-R | ATAATTGTCGTGGAAACAACGCCACTCATTTGTATATCAGCGTTGCATAGGCCACTAGTGGATCTG | SEQ ID NO 26 |
| CCP1-deletion-F | ATTTCGCATTCATGCAGACGCAAACACACGTATATCTACAATTCAGCTGAAGCTTCGTACGC | SEQ ID NO 27 |
| CCP1-deletion-R | AATAATACGAAATATAACCAATAAATAATATCTTTCCTCAGTGACGCATAGGCCACTACaGGATCTG | SEQ ID NO 28 |
| pPGI1-F | ATAAGAATGCGGCCGCTAACAAAAATCACGATCTGGGTGG | SEQ ID NO 29 |
| pPGI1-R | TTATCTCTCTTCAAAGTAGCCATTTTAGGCTGGTATCTTGATTCTAAA | SEQ ID NO 30 |
| TCYC1-F | AACTCATCATCACCATCACCATTAATAAGATCCGCTCTAACCGAAAAGG | SEQ ID NO 31 |
| TCYC1-R | AAACGAGCTCCTTCGAGCGTCCCAAAACCT | SEQ ID NO 32 |

Fatty Acid Decarboxylase Selection

Six more homologous enzymes from different organisms were selected for alkene biosynthesis in *S. cerevisiae* (Table 2). Among them, $oleT_{BS}$, $oleT_{MP}$ and $oleT_{CE}$ were reported to produce 1-pentadecene when heterologously expressed in *E. coli* [1]; $oleT_{SM}$, $oleT_{MC}$ and $OleT_{SP}$ were selected based on their protein sequence identity to $oleT_{JE}$, and their histidine residue in position 85 (His85) which as mentioned, plays an important role in catalysis activity of $OleT_{JE}$.

TABLE 2

OleT used in this study

| Name | Organism | Accession no. | Sequence ID No. |
|---|---|---|---|
| $OleT_{SM}$ | *Staphylococcus massiliensis* | WP_009381667 | SEQ ID NO 1 |
| $OleT_{MC}$ | *Macrococcus caseolyticus* JCSC5402 | YP_002560207 | SEQ ID NO 2 |
| $OleT_{SP}$ | *Staphylococcus pseudintermedius* ED99 | YP_006015679 | SEQ ID NO 3 |
| $OleT_{BS}$ | *Bacillus subtilis* 168 | NP_388092 | SEQ ID NO 4 |
| $OleT_{MP}$ | *Methylobacterium populi* BJ001 | ZP_02200540 | SEQ ID NO 5 |
| $OleT_{CE}$ | *Corynebacterium efficiens* YS-314 | NP_739069 | SEQ ID NO 6 |
| $OleT_{JE}$ | *Jeotgalicoccus sp.* ATCC 8456 | HQ709266 | SEQ ID NO 7 |

Plasmid Construction

To clone $oleT_{CE}$, genomic DNA of *Jeotgalicoccus* sp. ATCC 8456 was used as a PCR template performed with two primers $OleT_{JE}$-F and $OleT_{JE}$-R. One $oleT_{JE}$ codon optimized gene and six codon optimized $oleT_{CE}$ homologous genes, namely $oleT_{JE-CO}$, $oleT_{SM}$, $oleT_{SP}$, $oleT_{BS}$, $oleT_{MP}$, and $oleT_{CE}$, were synthesized from Life technologies. ACC1 and HEM3 were amplified from *S. cerevisiae* genome using two set of primers: ACC1-SC-F and ACC1-SC-R, Hem3-F and Hem3-R. A list of primers used was shown in Table 1. Plasmid pESC-URA (Agilent Technologies), pRS41K (Euroscarf) and pRS42K (Euroscarf) were used as expression vectors for oleT and/or ACC1 while plasmid pIS385 (Euroscarf) was used for HEM3 cloning. Either Gibson DNA assembly method [31] or digestion-ligation method was used for the construction of all the plasmids. The constructed recombinant plasmids are listed in Table 3.

TABLE 3

Strains and plasmids used in this study

| Strains or plasmids | Description | Source |
|---|---|---|
| Strains | | |
| *E. coli* Top10 | F' mcrA Δ(mrr-hsdRMS-mcrBC) φ80lacZΔM15 ΔlacX74 recA1 araD139 Δ(ara-leu) 7697 galU galK rpsL(Str$^R$) endA1 nupG | Invitrogen |
| *S. cerevisiae* | | |
| BY4741 | MATa his3Δ1 leu2Δ0 met15Δ0 ura3Δ0 | ATCC |
| BYSM | BY4741 with pESC-OleT$_{SM}$ | This study |
| BYMC | BY4741 with pESC-OleT$_{MC}$ | This study |
| BYSP | BY4741 with pESC-OleT$_{SP}$ | This study |
| BYBS | BY4741 with pESC-OleT$_{BS}$ | This study |
| BYCE | BY4741 with pESC-OleT$_{CE}$ | This study |
| BYJE | BY4741 with pESC-OleT$_{JE}$ | This study |
| BYFSM | BY4741, Δfaa1 Δfaa4 with pESC-OleT$_{SM}$ | This study |
| BYFMC | BY4741, Δfaa1 Δfaa4 with pESC-OleT$_{MC}$ | This study |
| BYFSP | BY4741, Δfaa1 Δfaa4 with pESC-OleT$_{SP}$ | This study |
| BYFBS | BY4741, Δfaa1 Δfaa4 with pESC-OleT$_{BS}$ | This study |
| BYFCE | BY4741, Δfaa1 Δfaa4 with pESC-OleT$_{CE}$ | This study |
| BYFJE | BY4741, Δfaa1 Δfaa4 with pESC-OleT$_{JE}$ | This study |
| BY10 | BY4741 with pESC-OleT$_{JE-CO}$ | This study |
| BY11 | BY4741 with pESC-OleT$_{JE-CO}$-ACC1 | This study |
| BY12 | BY4741, Δfaa1 with pESC-OleT$_{JE-CO}$ | This study |
| BY13 | BY4741, Δfaa4 with pESC-OleT$_{JE-CO}$ | This study |
| BY14 | BY4741, Δfaa1 Δfaa4 with pESC-OleT$_{JE-CO}$ | This study |
| BY15 | BY4741, Δfaa1 Δfaa4 P$_{TEF1}$-HEM3 with pESC-OleT$_{JE-CO}$ | This study |
| BY16 | BY4741, Δfaa1 Δfaa4 Δctt1 Δcta1 Δccp1 with pESC-OleT$_{JE-CO}$ | This study |
| BY17 | BY4741, Δfaa1 Δfaa4 Δctt1 Δcta1 Δccp1, P$_{TEF1}$-HEM3 with pESC-OleT$_{JE-CO}$ | This study |
| BY18 | BY4741, Δfaa1 Δfaa4 Δctt1 Δcta1 Δccp1, P$_{TEF1}$-HEM3 with pRS41K-P$_{GAL1}$-OleT$_{JE-CO}$ | This study |
| BY19 | BY4741, Δfaa1 Δfaa4 Δctt1 Δcta1 Δccp1, P$_{TEF1}$-HEM3 with pRS42K-P$_{GAL1}$-OleT$_{JE-CO}$ | This study |
| BY20 | BY4741, Δfaa1 Δfaa4 Δctt1 Δcta1 Δccp1, P$_{TEF1}$-HEM3 with pRS41K-P$_{PGH1}$-OleT$_{JE-CO}$ | This study |
| BY21 | BY4741, Δfaa1 Δfaa4 Δctt1 Δcta1 Δccp1, P$_{TEF1}$-HEM3 with pRS42K-P$_{PGH1}$-OleT$_{JE-CO}$ | This study |
| BY22 | BY4741, Δfaa1 Δfaa4 Δctt1 Δcta1 Δccp1, P$_{TEF1}$-HEM3 with pRS41K-P$_{TEF1}$-OleT$_{JE-CO}$ | This study |
| BY23 | BY4741, Δfaa1 Δfaa4 Δctt1 Δcta1 Δccp1, P$_{TEF1}$-HEM3 with pRS42K-P$_{TEF1}$-OleT$_{JE-CO}$ | This study |
| BY24 | BY4741, Δfaa1 Δfaa4 Δctt1 Δcta1 Δccp1, P$_{TEF1}$-HEM3, P$_{TEF1}$-OleT$_{JE-CO}$ | This study |
| Plasmids | | |
| pESC-URA | P$_{GAL1}$, P$_{GAL10}$ promoter, 2μ origin, AmpR, URA3 | Agilent Technologies |
| pIS385 | AmpR, URA3 | Euroscarf |
| pIS112 | AmpR, URA3 | Euroscarf |
| pUG6 | AmpR, kanMX | Euroscarf |
| pSH47 | CEN6/ARSH4 origin, CRE, AmpR, URA3 | Euroscarf |
| pRS41K | ARS/CEN origin, kanMX | Euroscarf |
| pRS42K | 2μ origin, kanMX | Euroscarf |
| pESC-OleT$_{JE}$ | pESC-URA carrying oleT$_{JE}$ under P$_{GAL1}$ control | This study |
| pESC-OleT$_{JE-CO}$ | pESC-URA carrying oleT$_{JE-CO}$ under P$_{GAL1}$ control | This study |
| pESC-OleT$_{SM}$ | pESC-URA carrying oleT$_{SM}$ under P$_{GAL1}$ control | This study |
| pESC-OleT$_{MC}$ | pESC-URA carrying oleT$_{MC}$ under P$_{GAL1}$ control | This study |
| pESC-OleT$_{SP}$ | pESC-URA carrying oleT$_{SP}$ under P$_{GAL1}$ control | This study |
| pESC-OleT$_{BS}$ | pESC-URA carrying oleT$_{BS}$ under P$_{GAL1}$ control | This study |
| pESC-OleT$_{MP}$ | pESC-URA carrying oleT$_{MP}$ under P$_{GAL1}$ control | This study |
| pESC-OleT$_{CE}$ | pESC-URA carrying oleT$_{CE}$ under P$_{GAL1}$ control | This study |
| pESC-OleT$_{JE-CO}$-ACC1 | pESC-URA carrying oleT$_{JE-CO}$ under P$_{GAL1}$ control and ACC1 under P$_{GAL10}$ control | This study |
| pRS41K-P$_{GAL1}$-OleT$_{JE-CO}$ | pRS41K carrying oleT$_{JE-CO}$ under P$_{GAL1}$ control | This study |
| pRS42K-P$_{GAL1}$-OleT$_{JE-CO}$ | pRS42K carrying oleT$_{JE-CO}$ under P$_{GAL1}$ control | This study |
| pRS41K-P$_{PGH1}$-OleT$_{JE-CO}$ | pRS41K carrying oleT$_{JE-CO}$ under P$_{PGH1}$ control | This study |
| pRS42K-P$_{PGH1}$-OleT$_{JE-CO}$ | pRS42K carrying oleT$_{JE-CO}$ under P$_{PGH1}$ control | This study |
| pRS41K-P$_{TEF1}$-OleT$_{JE-CO}$ | pRS41K carrying oleT$_{JE-CO}$ under P$_{TEF1}$ control | This study |
| pRS42K-P$_{TEF1}$-OleT$_{JE-CO}$ | pRS42K carrying oleT$_{JE-CO}$ under P$_{TEF1}$ control | This study |

Alkene Extraction and Detection

For alkene production, cells were pre-cultured in 10 ml medium overnight and then diluted in 50 ml induction medium using 250 ml flask to achieve an initial OD600 of 0.4. After growing for 48 h, yeast cells were harvested by centrifugation at 6000 g for 5 min. Cell pellets were re-suspended in HPLC grade methanol (Sigma), and 1-nonene was added into cell suspension as an internal standard. Acid-washed glass beads were added until the suspension was covered. Cells were then lysed by mechanical agitation using FastPrep-24 (MPBio) for 8 min at 6 m/s. HPLC grade hexane (Sigma) was then added and mixed thoroughly with crude extract for 5 min. The crude extract was separated into two phases by centrifugation, and the upper phase containing alkene was transferred into a clear GC vial.

The alkenes dissolved in the upper layer were quantified using gas chromatography-mass spectrometry (GC-MS) under the following conditions. An HP-5 ms column (30 m by 0.25 mm; 0.25 μm film; Agilent) was used with a helium flow rate set to 1.1 ml/min. Injections of 5 μl were carried out under splitless injection condition with the inlet set to 250° C. The GC temperature profile was as follows: an initial temperature of 40° C. was maintained for 0.5 min, followed by ramping to 280° C. at a rate of 6° C./min, where the temperature was held for 3 min. The mass spectrometer detector was scanned at 30 to 800 amu in the electron impact mode. To aid peak identification, authentic references (C9-C19 terminal alkenes, Tokyo Chemical Industry) were used, and their retention times and fragmentation patterns were compared with those from the extracted alkenes.

Bioreactor Conditions

Selected strain was used for production of alkenes through fed-batch fermentation. YPD+G418 containing 3% glucose was used for both seed preparation and fermentation. Seed culture was prepared by inoculating colonies into a 250 mL flask containing 50 mL culture medium, and incubating at 30° C. and 250 rpm for 24 h. The seed was then transferred to a 5 L bioreactor (BIOSTAT® B-DCU II, Sartorius) containing 1 L medium with an initial $OD_{600}$ 0.4. The fermentation was carried out at 30° C. The dissolved oxygen concentration in the bioreactor was maintained at around 60% by controlling the air flow rate and agitation speed. 150 ml 200 g/L glucose was fed to the fermenter every 24 h and samples were withdrawn at the indicated time intervals. All of the fermentation experiments were performed in triplicate.

Results

Screening Enzymes for Alkene Biosynthesis in S. cerevisiae

Figure 1B:
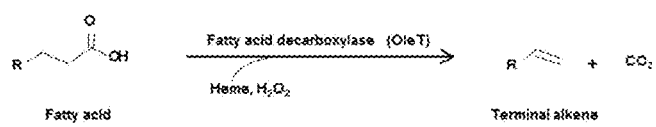
Figure 2:
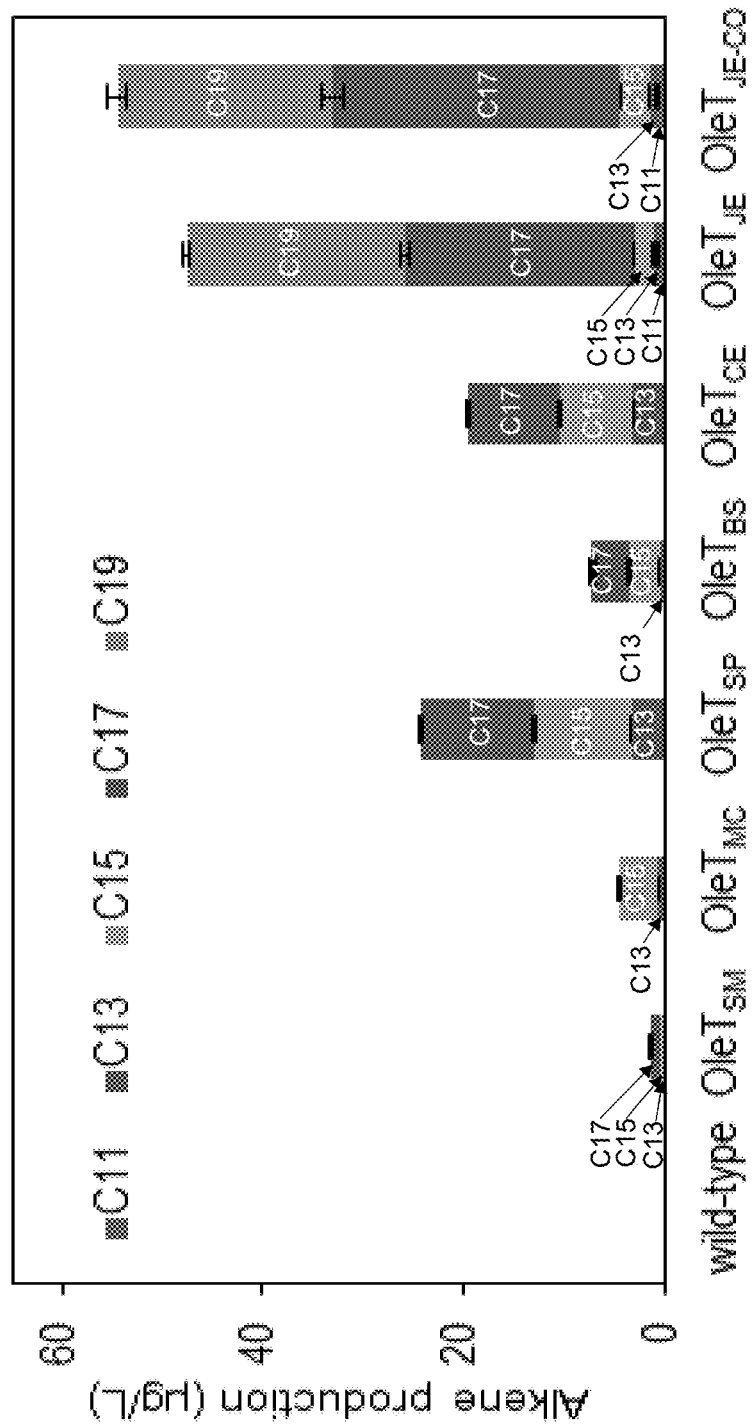
FIG. 2. Production of alkenes by recombinant *S. cerevisiae* expressing oleT$_{JE}$ homologs. Distributions of different chain length alkenes produced by the overexpression of oleT$_{SM}$, oleT$_{MC}$, oleT$_{SP}$, oleT$_{BS}$, oleT$_{CE}$, oleT$_{JE}$ and oleT$_{JE\text{-}co}$ are shown. Alkenes with different chain lengths from C11 to C19 are represented. Results are the average of three biological replicates with error bars showing the standard deviation from the mean value.

To enable terminal alkene production in S. cerevisiae, the inventors attempted to use the cytochrome P450 fatty acid decarboxylase $OleT_{JE}$ from Jeotgalicoccus sp. ATCC 8456, which reportedly decarboxylates fatty acids to terminal alkenes [1] (FIG. 1B). The inventors also used its codon-optimized version $oleT_{JE\text{-}CO}$ (SEQ ID NO 8) and six of its homologous genes, based on high sequence identity to $OleT_{JE}$ Table 2. Native $oleT_{JE}$ and synthesized codon-optimized homologous genes were cloned into the high copy plasmid pESC-URA (Table 3) and transformed into S. cerevisiae. The induced protein expression in S. cerevisiae was confirmed by western blot (data not shown). The inventors evaluated the performance of the abovementioned enzymes by quantifying the alkene profiles and measuring the alkene concentrations from the cell cultures grown for 48 h. The inventors found that the cells carrying the empty plasmid and $OleT_{MP}$ from Methylobacterium populi BJ001 produced no detectable alkenes (data not shown), whilst the transformants expressing the other OleT enzymes produced a range of alkenes. As shown in FIG. 2, $OleT_{SM}$, $OleT_{SP}$, $OleT_{BS}$ and $OleT_{CE}$ produced alkenes with the chain lengths of C13, C15 and C17, whereas $OleT_{MC}$ exhibited a narrower alkene profile, producing C13 and C15 alkenes. $OleT_{JE}$ and its codon-optimized version $OleT_{JE\text{-}CO}$ exhibited the broadest product profile range, producing odd chain terminal alkenes from C11 to C19. The inventors observed lower alkene titers for shorter chain lengths possibly because longer chain fatty acids are more abundant than shorter chain fatty acids in yeast cells [32].

Aside from the varying alkene profiles, the total titers of the produced alkenes varied among the tested OleT enzymes. FIG. 2 shows that $OleT_{SM}$ led to the lowest total alkene titer (1.4 μg/L), whereas $OleT_{JE\text{-}CO}$ gave the highest total alkene titer (54.5 μg/L), which served as the baseline titer for this study.

Increase in Free Fatty Acid Production Improved Alkene Production

As a first step in improving the alkene production, the inventors attempted to increase the production of free fatty acids, which are precursors to alkenes (FIG. 1A). The de novo fatty acid biosynthesis in S. cerevisiae requires acetyl-CoA carboxylase (ACC1; encoded by the ACC1) and fatty acid synthase complex (FAS; encoded by FAS1 and FAS2) [33-36]. ACC1 converts acetyl-CoA into malonyl-CoA, and the overexpression of ACC1 results in increase in final fatty acid level [33, 34]. The FAS complex produces fatty acyl-CoAs by condensation of one acetyl-CoA to 7-8 malonyl-CoAs [37]. The de novo produced fatty acyl-CoAs are further hydrolyzed to free fatty acids; however, free fatty acids are converted back to fatty acyl-CoAs by endogenous fatty acyl-CoA synthetase (FAA1-4, FAT1). As an active form of free fatty acids, fatty acyl-CoAs are further degraded mainly through (3-oxidation pathway (PDX1, FOX2, POT1). Hence, in order to enhance the metabolic flux towards free fatty acid, the inventors attempted to overexpress ACC1 and disrupt FAA1 and FAA4, the two main fatty acyl-CoA synthetases [38-40].

Figure 3A:
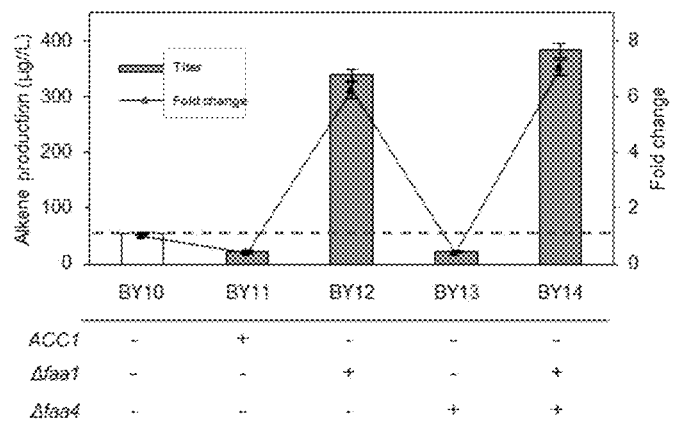
FIGS. 3A-3C. Effects of fatty acid pool engineering on alkene production.

First, the inventors expressed $oleT_{JE\text{-}CO}$ with ACC1 under the control of the strong inducible promoters $P_{GAL1}$ and $P_{GAL10}$, respectively, generating the strain BY11 (ACC1, $oleT_{JE\text{-}CO}$). Second, the inventors deleted FAA1 and/or FAA4, and expressed $oleT_{JE\text{-}CO}$, resulting in three different strains BY12 (Δfaa1, $oleT_{JE\text{-}CO}$), BY13 (Δfaa4, $oleT_{JE\text{-}CO}$), and BY14 (Δfaa1Δfaa4, $oleT_{JE\text{-}CO}$). As shown in FIG. 3A, the co-expression of ACC1 and $oleT_{JE\text{-}CO}$ in S. cerevisiae led to lower alkene levels compared with the singularly expressed $oleT_{JE\text{-}CO}$ (BY10, control strain). Moreover, increased alkene production levels were observed in both BY12 (6.2-fold) and BY14 (7-fold). In particular, the double-deletion strain BY14 produced the highest alkene titer of 382.8 μg/L. However, for an unknown reason, the single-deletion of FAA4 (BY13) led to 2.5-fold lower alkene production. These results suggest that the deletion of FAA1 in tandem with FAA4 has a synergic effect on fatty acid accumulation, where FAA1 accounts for most of this effect. In addition to the total alkene titers, changes in alkene profiles were also studied (Table 4).

TABLE 4

Comparison of alkene production obtained by engineered S. cerevisiae strains

| Strain | Alkene (fractional abundance %) | | | | | Total alkene (µg/L) |
|---|---|---|---|---|---|---|
| | C11 | C13 | C15 | C17 | C19 | |
| BYSM | — | 17.3 | 10.3 | 72.4 | — | 1.4 ± 0.3 |
| BYMC | — | 14.0 | 86.0 | — | — | 4.6 ± 0.1 |
| BYSP | — | 13.7 | 39.3 | 46.9 | — | 24.4 ± 0.3 |
| BYBS | — | 6.5 | 44.2 | 49.3 | — | 7.2 ± 0.4 |
| BYCE | — | 16.3 | 36.8 | 46.8 | — | 19.7 ± 0.3 |
| BYJE | 1.2 | 1.0 | 4.2 | 48.0 | 45.6 | 47.6 ± 0.8 |
| BYFSM | — | 2.6 | 13.1 | 84.3 | — | 75.0 ± 5.2 |
| BYFMC | — | 7.3 | 92.7 | — | — | 25.5 ± 0.3 |
| BYFSP | — | 3.1 | 41.1 | 55.8 | — | 121.2 ± 7.6 |
| BYFBS | — | 3.3 | 33.4 | 63.3 | — | 85.4 ± 4.7 |
| BYFCE | — | 2.3 | 36.8 | 61.0 | — | 129.6 ± 13.7 |
| BYFJE | 0.2 | 0.5 | 5.0 | 88.2 | 6.1 | 362.1 ± 3.0 |
| BY10 | 1.4 | 1.3 | 5.4 | 52.4 | 39.5 | 54.5 ± 2.2 |
| BY11 | — | 2.6 | — | 44.4 | 52.9 | 21.0 ± 2.3 |
| BY12 | — | 0.3 | 2.2 | 94.1 | 3.5 | 339.2 ± 10.8 |
| BY13 | — | 2.7 | 4.9 | 46.5 | 45.8 | 21.8 ± 2.0 |
| BY14 | 0.2 | 0.4 | 4.1 | 89.5 | 5.9 | 382.8 ± 12.6 |
| BY14[a] | 0.3 | 0.8 | 7.0 | 87.6 | 4.2 | 716.9 ± 30.0 |
| BY14[b] | 1.0 | 1.6 | 14.0 | 79.1 | 4.3 | 684.0 ± 27.5 |
| BY14[c] | 0.4 | 1.2 | 8.5 | 87.0 | 3.0 | 1387.4 ± 48.9 |
| BY15 | 0.1 | 0.3 | 3.7 | 92.2 | 3.7 | 403.8 ± 5.4 |
| BY16 | 0.1 | 0.4 | 4.3 | 91.1 | 4.2 | 402.0 ± 13.9 |
| BY17 | 0.2 | 0.3 | 3.1 | 92.5 | 3.8 | 472.7 ± 8.6 |
| BY18 | 0.2 | 1.1 | 8.3 | 77.2 | 13.2 | 1720.8 ± 156.9 |
| BY19 | 1.0 | 1.4 | 9.0 | 69.6 | 19.0 | 453.2 ± 29.8 |
| BY20 | 0.6 | 1.0 | 10.7 | 71.9 | 15.8 | 409.9 ± 25.9 |
| BY21 | 0.3 | 0.5 | 10.2 | 77.9 | 11.1 | 882.2 ± 195.4 |
| BY22 | 0.1 | 0.4 | 8.3 | 85.0 | 6.2 | 2088.7 ± 66.4 |
| BY23 | 0.6 | 0.9 | 9.5 | 59.6 | 29.4 | 551.9 ± 16.3 |
| BY24 | 0.6 | 0.8 | 8.7 | 70.2 | 19.7 | 450.8 ± 3.8 |
| BY22[d] | 0.4 | 0.3 | 5.8 | 52.1 | 41.4 | 763.9 ± 32.4 |
| BY22[e] | 1.0 | 0.3 | 4.4 | 82.0 | 12.2 | 2243.5 ± 117.3 |
| BY22[f] | 0.2 | 0.6 | 3.9 | 74.5 | 20.8 | 3289.1 ± 217.9 |
| BY22[g] | 0.6 | 0.7 | 5.6 | 58.6 | 34.5 | 3675.5 ± 218.4 |

Figure 3B:
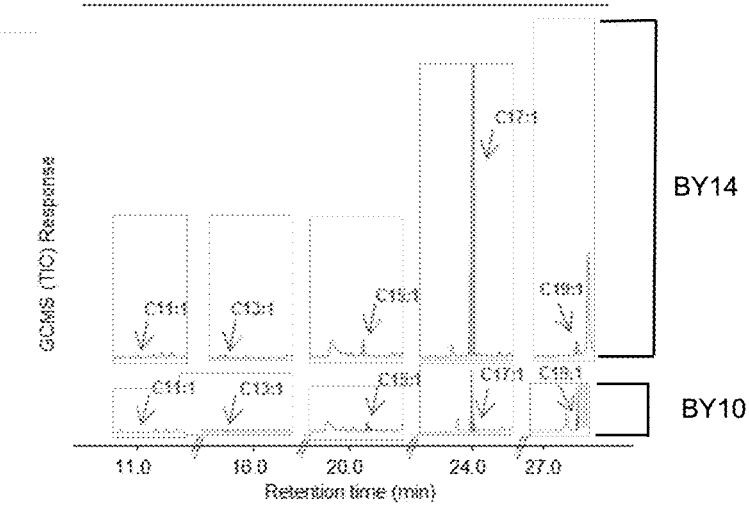
Figure 3C:
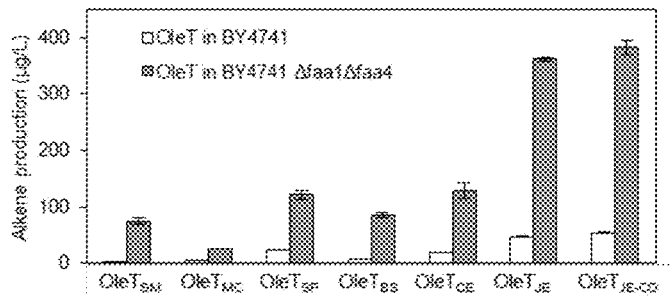

[a] Heme supplementation in medium
[b] $H_2O_2$ supplementation in medium
[c] Heme and $H_2O_2$ supplementation in medium
[d] 24 h growth in bioreactor
[e] 48 h growth in bioreactor
[f] 72 h growth in bioreactor
[g] 144 h growth in bioreactor
—: not detected As shown in the gas chromatography (GC) profile, BY14 showed a significant improvement in the production of C15 and C17 alkenes compared to BY10, but a lower improvement for other alkenes (FIG. 3B). This increase in the production of C15 and C17 alkenes could be attributed to that BY14 accumulated more C16 and C18 free fatty acids (data not shown). The inventors then expressed all eight OleT enzymes in the double-deletion strain (Δfaa1Δfaa4), respectively, and evaluated the alkene titers. The inventors found that the overexpression of $oleT_{JE-CO}$ showed the highest total alkene titer in the double-deletion strain (Δfaa1Δfaa4) (FIG. 3C), in line with the result from the overexpression of $oleT_{JE-CO}$ in the wild-type strain. Thus, the inventors selected BY14 (Δfaa1Δfaa4, $oleT_{JE-CO}$) for further engineering, which showed a 7-fold improvement in the titer to the control alkene-producing strain BY10 ($oleT_{JE-CO}$).

Cofactor Engineering Further Increased Alkene Production Level

1) Supplementation of Cofactors: Heme and Hydrogen Peroxide

The inventors then improved the enzyme cofactor availability to further increase the associated metabolic flux towards alkene production. $OleT_{JE}$ is a cytochrome P450 enzyme in the cyp152 family, which contains heme as a cofactor [1], and the overexpression of cytochrome P450 enzymes can lead to heme depletion [41]. Further, $OleT_{JE}$ is highly active in the presence of hydrogen peroxide which serves as the sole electron and oxygen donor [1]. Therefore, the inventors hypothesized that cellular depletion of heme and hydrogen peroxide resulting from the overexpression of the P450 enzyme $OleT_{JE}$ could be a limiting factor, and thus, increasing the availability of the two cofactors heme and hydrogen peroxide might improve alkene synthesis.

Figure 4:
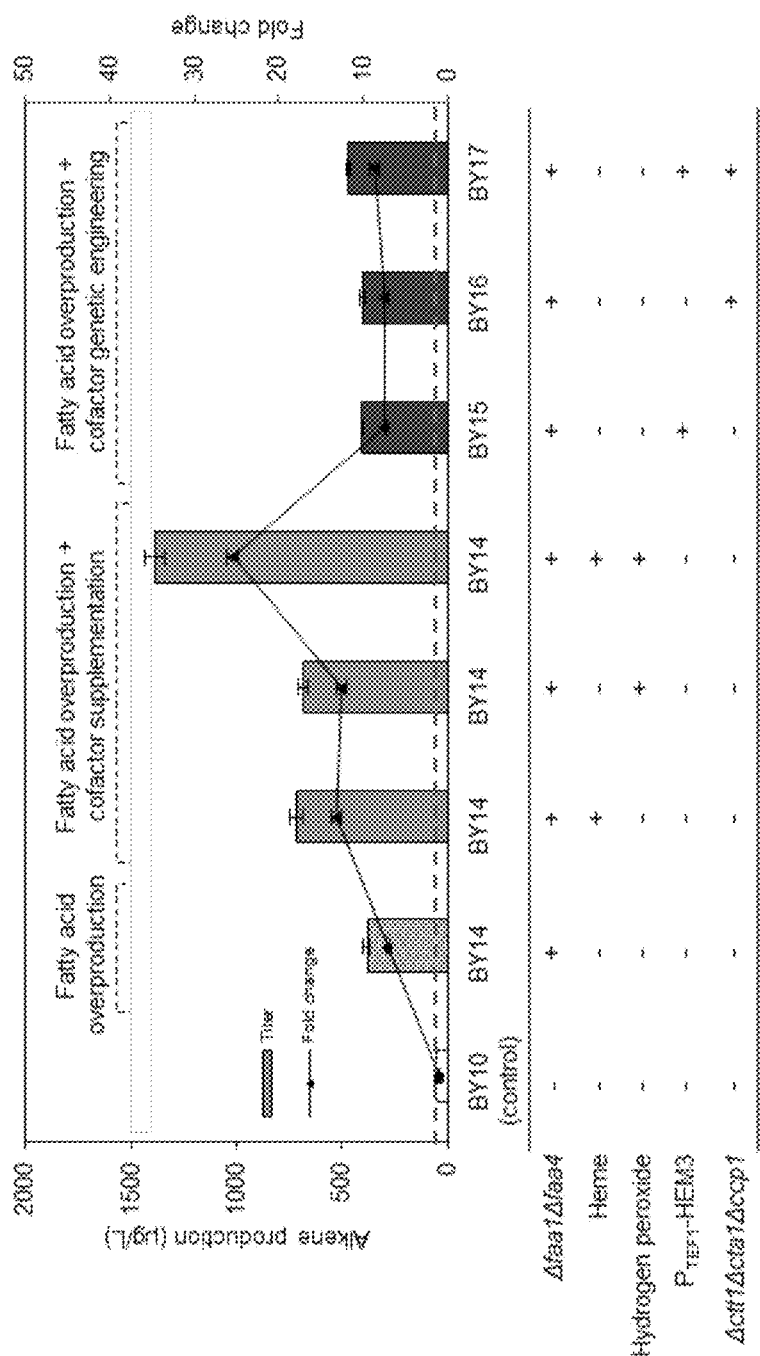
FIG. 4. Production of alkenes by cofactor engineering. Total alkene titers are shown in bars and alkene fold changes are shown in lines. White bars and grey horizontal dash lines indicate the alkene titers of the control strain BY10. Lattice bars represent samples with fatty acid overproduction; Grey color bars represent samples with fatty acid overproduction and cofactor supplementation; Black color bars represent samples with fatty acid overproduction and cofactor genetic engineering. For alkene fold changes, BY10 was set equal to 1.0 and all values were determined relative to BY10. "+" and "−" indicate with and without engineering respectively. Error bars represent the standard deviation of three biological replicates.

To test this hypothesis, the inventors supplemented BY14 (Δfaa1Δfaa4, $oleT_{JE-CO}$) with heme, hydrogen peroxide, or both. As shown in FIG. 4, the supplementation with heme, hydrogen peroxide or both increased the titer by 87%, 79%, and 3.6-fold respectively, with the highest production at 1.4 mg/L. The improved alkene production demonstrated that cofactors supplementation during OleT enzyme expression could be employed to boost the alkene titers.

2) Overexpression of HEM3, and Triple-Deletion of CTT1, CTA1 and CCP1

Based on the abovementioned result from the cofactor supplementation, the inventors attempted to increase the alkene titer using genetic cofactor engineering to eliminate the need for cofactor supplementation, which could be costly. The inventors first aimed to improve cellular heme production, which could be achieved by overexpression of rate-limiting enzymes responsible for heme biosynthesis. Multiple enzymes are involved in the heme biosynthesis pathway including three rate-limiting enzymes, HEM2, HEM3 and HEM12 [42]; however, the co-expression of these three HEM enzymes could be stressful to the host cells [41]. For example, the strains expressing only HEM3 exhibited no growth defect, and in combination with expression of P450 enzyme, showed high theophylline titers [41]. Therefore, in this study, HEM3 was integrated into genome and constitutively expressed under the control of TEF1 promoter, referred to as strain BY15 (Δfaa1Δfaa4, $P_{TEF1}$-HEM3, $oleT_{JE-CO}$). Secondly, the inventors aimed to accumulate endogenous hydrogen peroxide by deleting its utilization enzymes, catalase T (CTT1) located in cytoplasm, catalase A (CTA1) located in peroxisomes [43], and the antioxidant enzyme cytochrome c peroxidase (CCP1) located in mitochondria [44]. Previous studies showed that increased levels of hydrogen peroxide were detected in catalase mutants and cells with chemically inactivated catalases [45, 46]. Hence, the inventors further deleted CTT1, CTA1 and CCP1 genes to generate a series of deletion strains that could improve cofactor availability (Table 3).

As shown in FIG. 4, HEM3 expression (BY15) brought a slight improvement in the total alkene titer compared to BY14 (without HEM3 overexpression). However, among all the deletion mutants, only BY16 (Δfaa1Δfaa4Δctt1Δcta1Δccp1, $oleT_{JE-CO}$) showed a slightly higher titer compared to BY14 (Δfaa1Δfaa4, $oleT_{JE-CO}$), while the rest deletion mutants showed no improved alkene titers (data not shown). To examine the potential synergistic effect of the aforementioned two approaches, the inventors integrated HEM3 into the genome of BY16, resulting in BY17 (Δfaa1Δfaa4Δctt1Δcta1Δccp1, $P_{TEF1}$-HEM3, $oleT_{JE-CO}$). As shown in FIG. 4, BY17 (Δfaa1Δfaa4Δctt1Δcta1Δccp1, $P_{TEF1}$-HEM3, $oleT_{JE-CO}$) produced a total alkene titer of 472.7 µg/L, 23% improvement to the fatty acid-overproducing strain BY14 (Δfaa1Δfaa4, $oleT_{JE-CO}$) and 8.7-fold improvement to the control strain BY10 ($oleT_{JE-CO}$).

Gene Expression Tuning for Alkene Production in Rich Medium

The inventors then enhanced the cell growth in rich medium and tuned the expression level of the heterologous genes. In the highest producing strain so far BY17, the oleT$_{JE-CO}$ was placed under the control of the galactose inducible promoter P$_{GAL1}$ on the high-copy plasmid pESC-URA containing the auxotrophic URA marker. Rich medium frequently increase cell growth and final cell amount, resulting in higher product titers [47]. Thus, here the inventors replaced the auxotrophic pESC-URA plasmid with pRS plasmids containing the KanMX resistance marker. Moreover, to optimize the expression level of the heterologous genes, the inventors used pRS41K (low copy) and pRS42K (high copy) as cloning vectors [48]. P$_{GAL1}$ (a strong inducible promoter), Ppm (a weak constitutive promoter) and P$_{TEF1}$ (a strong constitutive promoter) were employed in both vectors to modulate the oleT$_{JE-CO}$ transcription. A total of six engineered strains were constructed and tested for alkene production (Table 3).

Figure 5:
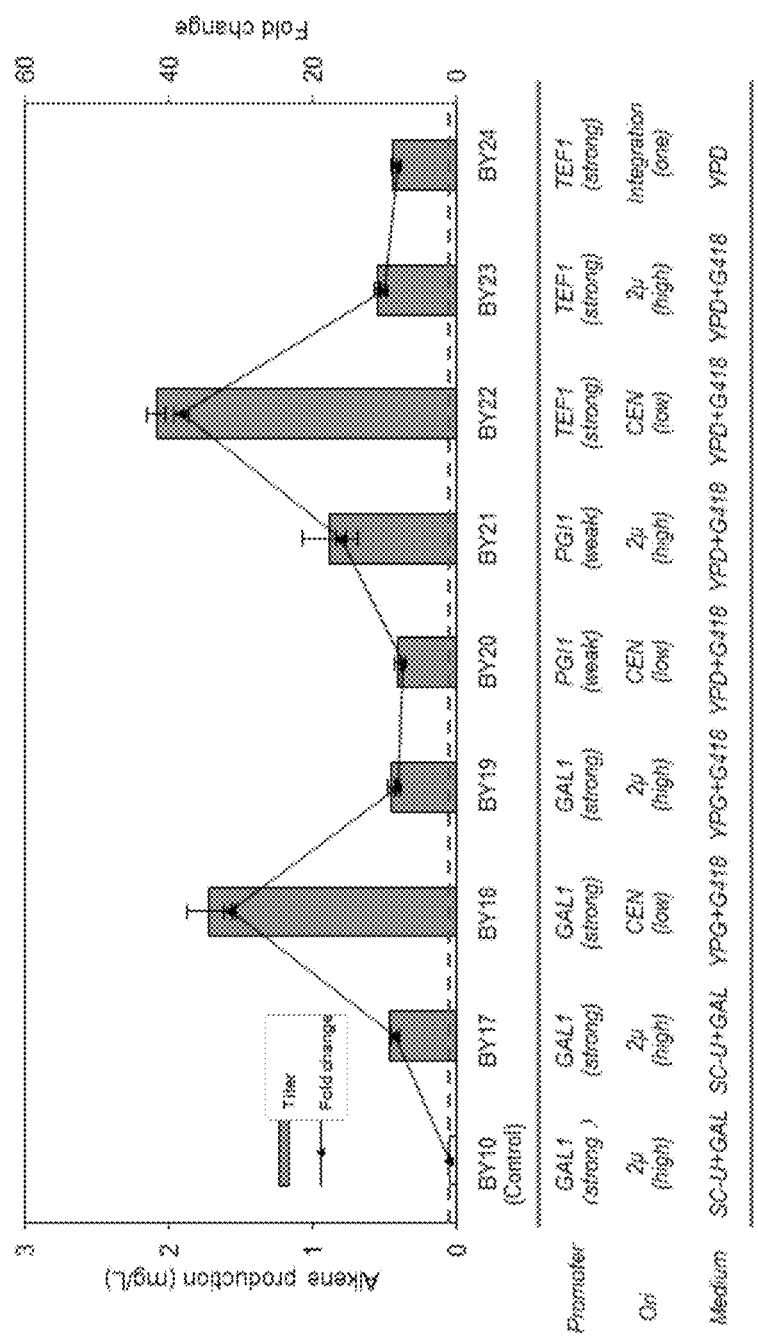
FIG. 5. Alkene production using strains with tuned gene expression in rich medium. Total alkene titers are shown in bars and alkene fold changes are shown in lines. White bar and grey horizontal dash line indicates the alkene titers of control strain BY10. For alkene fold change, BY10 was set equal to 1.0 and all values were determined relative to BY10. Promoter strengths, plasmid copy numbers and respective growth medium are listed for each sample. Data shown are the mean±SD of three biological replicates.

All the engineered oleT$_{JE-CO}$ containing strains were cultivated in rich medium supplied with 2% galactose or glucose for alkene production. The inventors found that all the engineered strains exhibited increased cell growth and much higher final cell amount, where OD$_{600}$~30 was achieved in the rich medium while OD$_{600}$~8 in the minimal medium). As shown in FIG. 5, among the abovementioned six constructed strains, BY22 (Δfaa1Δfaa4Δctt1Δcta1Δccp1, P$_{TEF1}$-HEM3, P$_{TEF1}$-oleT$_{JE-CO}$ (pRS41K)), which contains the strong constitutive promoter P$_{TEF1}$ on the low copy plasmid pRS41K, showed the highest alkene production, 2.1 mg/L, 4.4-fold higher than BY17 and 38.3-fold higher than the control strain BY10. The strains containing oleT$_{JE-CO}$ under the control of the weak promoter Ppm showed 2.2-fold higher alkene production on the high copy plasmid pRS42K (BY21) than that on the low copy plasmid pRS41K (BY20). This result indicates that sufficient expression of oleT$_{JE-CO}$ is needed for relatively higher alkene production. In contrast, with the strong promoter P$_{GAL1}$ or P$_{TEF1}$, the strains with the high copy plasmid (BY19 and BY23) showed 3.8-fold lower alkene production compared with the strains with the low copy plasmid (BY18 and BY22). These results suggest that in our study, i) the use of a strong promoter on a low copy plasmid provided sufficient enzyme levels for alkene production and ii) the use of a strong promoter on a high copy plasmid might cause "metabolic burden" on the cell, making the overall process non-beneficial [49]. To further address the "plasmid burden" [50] and to avoid the antibiotics cost, oleT$_{JE-CO}$ was chromosomally integrated and constitutively expressed under the TEF1 promoter. This constructed strain BY24 (Δfaa1Δfaa4Δctt1Δcta1Δccp1, P$_{TEF1}$-HEM3, P$_{TEF1}$-oleT$_{JE-CO}$) produced about 4.6-fold less alkene than BY22 harboring oleT$_{JE-CO}$ on a low-copy plasmid, suggesting that a single copy of oleT$_{JE-CO}$ likely brought about insufficient gene expression level.

Bioreactor Process Optimization for Higher Alkene Production

The inventors then conducted fed-batch fermentation and optimized the fermentation conditions to achieve higher alkene production. The inventors used BY22 (Δfaa1Δfaa4Δctt1Δcta1Δccp1, P$_{TEF1}$-HEM3, P$_{TEF1}$-oleT$_{JE-CO}$ (pRS41K)), the highest alkene production strain so far in shake flask culture, to test in fed-batch bioreactors. Three parameters, temperature, pH and dissolved oxygen concentration (pO2), were controlled and monitored. Three different operation temperatures, 25° C., 30° C. and 35° C. gave comparable alkene titers (data not shown). pH 5, pH 7 and pH off were tested, where pH off showed a higher alkene titer (data not shown). Since heme biosynthesis requires oxygen [42] and an aerobic condition could give higher cell growth, the pO2 level was maintained at around 60% saturation, a general aerobic condition for yeast growth. Thus, the inventors chose temperature 30° C., pH off and pO$_2$ 60% as our operation condition.

Figures 6A, 6B:
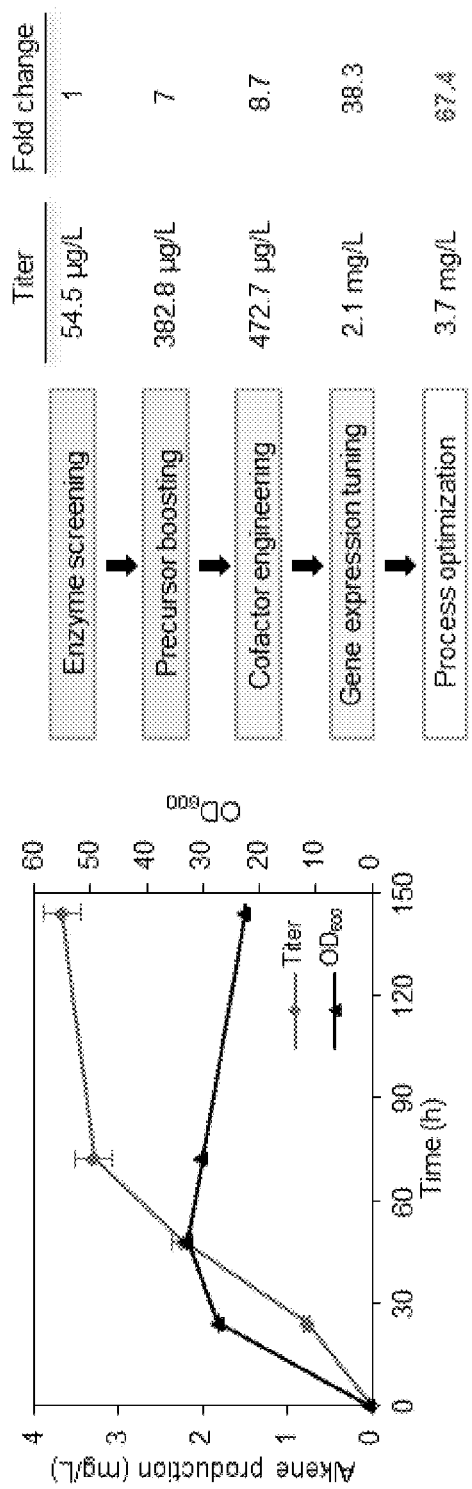
FIGS. 6A-6B.

As shown in FIG. 6A, during the first 48 h, BY22 grew steadily and the levels of the produced alkene were increased to 2.2 mg/L. After 48 h, strain went through the stationary phase, and the alkene levels were further increased from 2.2 mg/L to 3.3 mg/L at 72 h; however, longer incubations only marginally increased alkene levels. These growth conditions gave rise to the highest level of production at 144 h, resulting in the alkene titer of 3.7 mg/L, 1.8-fold increase to the shake flask condition and 67.4-fold increase to the control strain BY10. Finally, FIG. 6B and Table 4 summarize the abovementioned sequential improvements in the alkene production through enzyme screening, precursor boosting, cofactor engineering, gene expression tuning and process optimization.

CONCLUSIONS

In this study, the inventors engineered *S. cerevisiae* to produce terminal alkene and further improved the alkene production 67.4-fold by combinatorial engineering strategies. First, OleT$_{JE}$ and its homologous enzymes were characterized to convert free fatty acids into alkenes. In particular, OleT$_{JE-CO}$ (codon optimized OleT from *Jeotgalicoccus* sp.) showed the broadest alkene profiles and the highest production level. Second, the deletion of both FAA1 and FAA4 significantly improved the alkene titer, likely due to increased free fatty acid pool. Third, genetic cofactor engineering involving the overexpression of HEM3 and the triple-deletion of CTT1, CTA1 and CCP1 further improved the alkene titer. Fourth, the tuning of the heterologous gene expression in the rich medium enabled a further improvement in the titer (i.e. BY22 (Δfaa1Δfaa4Δctt1Δcta1Δccp1, P$_{TEF1}$-HEM3, P$_{TEF1}$-oleT$_{JE-CO}$ (pRS41K)). Finally, the optimization of the culturing conditions in fed-batch bioreactors further improved the alkene production in BY22. This study represents the first report of terminal alkene biosynthesis in the yeast *S. cerevisiae*, and taken together, the abovementioned combinatorial engineering approaches increased the titer of the alkene production of *S. cerevisiae* 67.4-fold. The inventors envision that these approaches could provide insights into devising engineering strategies to improve the production of fatty acid-derived biochemicals in *S. cerevisiae*.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

REFERENCES

[1] M. A. Rude, T. S. Baron, S. Brubaker, M. Alibhai, S. B. Del Cardayre, and A. Schirmer, "Terminal Olefin (1-Alkene) Biosynthesis by a Novel P450 Fatty Acid Decarboxylase from *Jeotgalicoccus* Species," Applied and Environmental Microbiology, vol. 77, pp. 1718-1727, Mar. 1, 2011 2011.

[2] Y. Liu, C. Wang, J. Yan, W. Zhang, W. Guan, X. Lu, and S. Li, "Hydrogen peroxide-independent production of alpha-alkenes by OleTJE P450 fatty acid decarboxylase," Biotechnology for Biofuels, vol. 7, p. 28, 2014.

[3] J. Belcher, K. J. McLean, S. Matthews, L. S. Woodward, K. Fisher, S. E. J. Rigby, D. R. Nelson, D. Potts, M. T. Baynham, D. A. Parker, D. Leys, and A. W. Munro, "Structure and Biochemical Properties of the Alkene Producing Cytochrome P450 OleTJE (CYP152L1) from the *Jeotgalicoccus* sp. 8456 Bacterium," Journal of Biological Chemistry, vol. 289, pp. 6535-6550, Mar. 7, 2014 2014.

[4] B. de Jong, V. Siewers, and J. Nielsen, "Systems biology of yeast: enabling technology for development of cell factories for production of advanced biofuels," Current opinion in biotechnology, Dec. 12 2011.

[5] F. Zhang, S. Rodriguez, and J. D. Keasling, "Metabolic engineering of microbial pathways for advanced biofuels production," Current opinion in biotechnology, vol. 22, pp. 775-783, 2011.

[6] P. P. Peralta-Yahya, F. Zhang, S. B. del Cardayre, and J. D. Keasling, "Microbial engineering for the production of advanced biofuels," Nature, vol. 488, pp. 320-328, 2012.

[7] G. Stephanopoulos, "Synthetic Biology and Metabolic Engineering," ACS Synthetic Biology, vol. 1, pp. 514-525, 2012/11/16 2012.

[8] D. Wang, S. H. Hakim, D. Martin Alonso, and J. A. Dumesic, "A highly selective route to linear alpha olefins from biomass-derived lactones and unsaturated acids," Chemical Communications, vol. 49, pp. 7040-7042, 2013.

[9] M. A. Poirier and A. E. George, "Selective separation and identification of olefins in petroleum and synthetic fuel naphtha," Fuel, vol. 61, pp. 182-184, 1982.

[10] T. P. Howard, S. Middelhaufe, K. Moore, C. Edner, D. M. Kolak, G. N. Taylor, D. A. Parker, R. Lee, N. Smirnoff, S. J. Ayes, and J. Love, "Synthesis of customized petroleum-replica fuel molecules by targeted modification of free fatty acid pools in *Escherichia coli*," Proceedings of the National Academy of Sciences, Apr. 22, 2013 2013.

[11] D. Mendez-Perez, M. B. Begemann, and B. F. Pfleger, "Modular Synthase-Encoding Gene Involved in α-Olefin Biosynthesis in *Synechococcus* sp. Strain PCC 7002," Applied and Environmental Microbiology, vol. 77, pp. 4264-4267, Jun. 15, 2011 2011.

[12] H. R. Beller, E.-B. Goh, and J. D. Keasling, "Genes Involved in Long-Chain Alkene Biosynthesis in *Micrococcus luteus*," Applied and Environmental Microbiology, vol. 76, pp. 1212-1223, Feb. 15, 2010 2010.

[13] D. J. Sukovich, J. L. Seffernick, J. E. Richman, J. A. Gralnick, and L. P. Wackett, "Widespread Head-to-Head Hydrocarbon Biosynthesis in Bacteria and Role of OleA," Applied and Environmental Microbiology, vol. 76, pp. 3850-3862, Jun. 15, 2010 2010.

[14] D. J. Sukovich, J. L. Seffernick, J. E. Richman, K. A. Hunt, J. A. Gralnick, and L. P. Wackett, "Structure, Function, and Insights into the Biosynthesis of a Head-to-Head Hydrocarbon in *Shewanella oneidensis* Strain MR-1," Applied and Environmental Microbiology, vol. 76, pp. 3842-3849, Jun. 15, 2010 2010.

[15] H. Ogiwara, T. Tanabe, J.-i. Nikawa, and S. Numa, "Inhibition of Rat-Liver Acetyl-Coenzyme-A Carboxylase by Palmitoyl-Coenzyme A," European Journal of Biochemistry, vol. 89, pp. 33-41, 1978.

[16] M. S. Davis and J. E. Cronan, "Inhibition of *Escherichia coli*Acetyl Coenzyme A Carboxylase by Acyl-Acyl Carrier Protein," Journal of Bacteriology, vol. 183, pp. 1499-1503, Feb. 15, 2001 2001.

[17] L. Kizer, D. J. Pitera, B. F. Pfleger, and J. D. Keasling, "Application of Functional Genomics to Pathway Optimization for Increased Isoprenoid Production," Applied and Environmental Microbiology, vol. 74, pp. 3229-3241, May 15, 2008 2008.

[18] R. J. Conrado, G. C. Wu, J. T. Boock, H. Xu, S. Y. Chen, T. Lebar, J. Turnšek, N. Tomšič, M. Avbelj, R. Gaber, T. Koprivnjak, J. Mori, V. Glavnik, I. Vovk, M. Benčina, V. Hodnik, G. Anderluh, J. E. Dueber, R. Jerala, and M. P. DeLisa, "DNA-guided assembly of biosynthetic pathways promotes improved catalytic efficiency," Nucleic Acids Research, vol. 40, pp. 1879-1889, Feb. 1, 2012 2012.

[19] D. J. Pitera, C. J. Paddon, J. D. Newman, and J. D. Keasling, "Balancing a heterologous mevalonate pathway for improved isoprenoid production in *Escherichia coli*," Metabolic Engineering, vol. 9, pp. 193-207, 2007.

[20] K. O. Yu, S. W. Kim, and S. O. Han, "Engineering of glycerol utilization pathway for ethanol production by *Saccharomyces cerevisiae*," Bioresource Technology, vol. 101, pp. 4157-4161, 2010.

[21] C. Leber and N. A. Da Silva, "Engineering of *Saccharomyces cerevisiae* for the synthesis of short chain fatty acids," Biotechnology and bioengineering, pp. n/a-n/a, 2013.

[22] E. Nevoigt, "Progress in Metabolic Engineering of *Saccharomyces cerevisiae*," Microbiology and Molecular Biology Reviews, vol. 72, pp. 379-412, Sep. 1, 2008 2008.

[23] R. Kalscheuer, H. Luftmann, and A. Steinbuchel, "Synthesis of Novel Lipids in *Saccharomyces cerevisiae* by Heterologous Expression of an Unspecific Bacterial Acyltransferase," Applied and Environmental Microbiology, vol. 70, pp. 7119-7125, 2004.

[24] F. Lopez de Felipe, M. Kleerebezem, W. M. de Vos, and J. Hugenholtz, "Cofactor Engineering: a Novel Approach to Metabolic Engineering in *Lactococcus lactis* by Controlled Expression of NADH Oxidase," Journal of Bacteriology, vol. 180, pp. 3804-3808, Aug. 1, 1998 1998.

[25] G. Scalcinati, S. Partow, V. Siewers, M. Schalk, L. Daviet, and J. Nielsen, "Combined metabolic engineering of precursor and co-factor supply to increase alpha-santalene production by *Saccharomyces cerevisiae*," Microbial cell factories, vol. 11, p. 117, 2012.

[26] J.-Y. Cho and T. W. Jeffries, "Transcriptional Control of ADH Genes in the Xylose-Fermenting Yeast *Pichia stipitis*," Applied and Environmental Microbiology, vol. 65, pp. 2363-2368, Jun. 1, 1999 1999.

[27] D. M. Villarreal, C. L. Phillips, A. M. Kelley, S. Villarreal, A. Villaloboz, P. Hernandez, J. S. Olson, and D. P. Henderson, "Enhancement of Recombinant Hemoglobin Production in *Escherichia coli* BL21(DE3) Containing the *Plesiomonas shigelloides* Heme Transport System," Applied and Environmental Microbiology, vol. 74, pp. 5854-5856, Sep. 15, 2008 2008.

[28] S. Izawa, Y. Inoue, and A. Kimura, "Importance of catalase in the adaptive response to hydrogen peroxide: analysis of acatalasaemic *Saccharomyces cerevisiae*," Biochem. J., vol. 320, pp. 61-67, Nov. 15, 1996 1996.

[29] U. Güldener, S. Heck, T. Fiedler, J. Beinhauer, and J. H. Hegemann, "A New Efficient Gene Disruption Cassette for Repeated Use in Budding Yeast," Nucleic Acids Research, vol. 24, pp. 2519-2524, Jul. 1, 1996 1996.

[30] I. Sadowski, T.-C. Su, and J. Parent, "Disintegrator vectors for single-copy yeast chromosomal integration," Yeast, vol. 24, pp. 447-455, 2007.

[31] D. G. Gibson, L. Young, R.-Y. Chuang, J. C. Venter, C. A. Hutchison, and H. O. Smith, "Enzymatic assembly of DNA molecules up to several hundred kilobases," Nat Meth, vol. 6, pp. 343-345, 2009.

[32] J. W. Welch and A. L. Burlingame, "Very Long-Chain Fatty Acids in Yeast," Journal of Bacteriology, vol. 115, pp. 464-466, Jul. 1, 1973 1973.

[33] M. Tai and G. Stephanopoulos, "Engineering the push and pull of lipid biosynthesis in oleaginous yeast *Yarrowia lipolytica* for biofuel production," Metabolic Engineering, vol. 15, pp. 1-9, 2013.

[34] R. Ruenwai, S. Cheevadhanarak, and K. Laoteng, "Overexpression of Acetyl-CoA Carboxylase Gene of *Mucor rouxii* Enhanced Fatty Acid Content in *Hansenula polymorpha*," Molecular Biotechnology, vol. 42, pp. 327-332, 2009/07/01 2009.

[35] G.-H. Shin, M. Veen, U. Stahl, and C. Lang, "Overexpression of genes of the fatty acid biosynthetic pathway leads to accumulation of sterols in *Saccharomyces cerevisiae*," Yeast, vol. 29, pp. 371-383, 2012.

[36] W. Runguphan and J. D. Keasling, "Metabolic engineering of *Saccharomyces cerevisiae* for production of fatty acid-derived biofuels and chemicals," Metabolic Engineering.

[37] 0. Tehlivets, K. Scheuringer, and S. D. Kohlwein, "Fatty acid synthesis and elongation in yeast," Biochimica et Biophysica Acta (BBA)—Molecular and Cell Biology of Lipids, vol. 1771, pp. 255-270, 2007.

[38] P. N. Black and C. C. DiRusso, "Yeast acyl-CoA synthetases at the crossroads of fatty acid metabolism and regulation," Biochimica et Biophysica Acta (BBA)—Molecular and Cell Biology of Lipids, vol. 1771, pp. 286-298, 2007.

[39] J.-Y. Choi and C. E. Martin, "The *Saccharomyces cerevisiae* FAT1 Gene Encodes an Acyl-CoA Synthetase That Is Required for Maintenance of Very Long Chain Fatty Acid Levels," Journal of Biological Chemistry, vol. 274, pp. 4671-4683, Feb. 19, 1999 1999.

[40] M. Scharnewski, P. Pongdontri, G. Mora, M. Hoppert, and M. Fulda, "Mutants of *Saccharomyces cerevisiae* deficient in acyl-CoA synthetases secrete fatty acids due to interrupted fatty acid recycling," The FEBS journal, vol. 275, pp. 2765-78, June 2008.

[41] J. K. Michener, J. Nielsen, and C. D. Smolke, "Identification and treatment of heme depletion attributed to overexpression of a lineage of evolved P450 monooxygenases," Proceedings of the National Academy of Sciences, vol. 109, pp. 19504-19509, Nov. 20, 2012 2012.

[42] M. Hoffman, M. Göra, and J. Rytka, "Identification of rate-limiting steps in yeast heme biosynthesis," Biochemical and biophysical research communications, vol. 310, pp. 1247-1253, 2003.

[43] V. Y. Petrova, T. V. Rasheva, and A. V. Kujumdzieva, Catalase enzyme in mitochondria of *Saccharomyces cerevisiae*, 2002.

[44] C. Verduyn, M. L. F. Giuseppin, W. A. Scheffers, and J. P. van Dijken, "Hydrogen Peroxide Metabolism in Yeasts," Applied and Environmental Microbiology, vol. 54, pp. 2086-2090, Aug. 1, 1988 1988.

[45] A. Mesquita, M. Weinberger, A. Silva, B. Sampaio-Marques, B. Almeida, C. Leão, V. Costa, F. Rodrigues, W. C. Burhans, and P. Ludovico, "Caloric restriction or catalase inactivation extends yeast chronological lifespan by inducing H2O2 and superoxide dismutase activity," Proceedings of the National Academy of Sciences, vol. 107, pp. 15123-15128, Aug. 24, 2010 2010.

[46] M. Zhang and H. Y. Wang, "Hydrogen peroxide production using chemically treated *Pichia pastoris* cells," Enzyme and Microbial Technology, vol. 16, pp. 10-17, 1994.

[47] B. Hahn-Hagerdal, K. Karhumaa, C. Larsson, M. Gorwa-Grauslund, J. Gorgens, and W. van Zyl, "Role of cultivation media in the development of yeast strains for large scale industrial use," Microbial cell factories, vol. 4, p. 31, 2005.

[48] Z. Wang, C. Gao, Q. Wang, Q. Liang, and Q. Qi, "Production of pyruvate in *Saccharomyces cerevisiae* through adaptive evolution and rational cofactor metabolic engineering," Biochemical Engineering Journal, vol. 67, pp. 126-131, 2012.

[49] S. Ostergaard, L. Olsson, and J. Nielsen, "Metabolic Engineering of *Saccharomyces cerevisiae*," Microbiology and Molecular Biology Reviews, vol. 64, pp. 34-50, Mar. 1, 2000 2000.

[50] A. S. Karim, K. A. Curran, and H. S. Alper, "Characterization of plasmid burden and copy number in *Saccharomyces cerevisiae* for optimization of metabolic engineering applications," FEMS yeast research, vol. 13, pp. 107-116, 2013.

SEQUENCES $OleT_{SM}$ (SEQ ID NO 1):
```
ATGTTCGTCGATTCCATCTTGGTCTTGAGATTGAACTTGTTGAAAACCGGTATACAAT
TGGAAATGAAGAACGGTGGTATTAAGGTTGCTAAGAAATTGCCAAAGGTTAAGGGT
TTGGATAACACCGTTGATATCATTAAGGGTGGTTACACTTACGTTCCAGGTAAGTTG
GAAGAATTCGATTCTAAGGCTTTCGAAGTTAGAGCTTTGGGTGGTAAAAAGATTGCT
GTCATGTCTGGTAAAGAAGCCGCTGAAATTTTCTACGACAACGAAAAGATGGAAAG
ACAAGGTACTTTGCCAAAGAGAATCGTTAACACTTTGTTTGGTAAGGGTGCTATTCA
TACCACTGCTGGTAAAAAACACGTTGATAGAAAGGCCTTGTTCATGTCTTTGATGAC
TGACGAAAACTTGAACTACTTGAGAGAATTGACCAGAAACTACTGGTTTATGAACA
CCGAAAGAATGCAATCCATGGACAAGGTTAACGTCTACAACGAATCTATCTACATGT
TGACCAAGATCGGTTTTAGATGGGCCGGTATTATTCAAACTCCTGAAGAAGCTGAAC
AAAACGCTAAAGATATGGACACCATGATCAACTCATTCGTCAGTTTGGGTTCTGCTT
ACAAAGGTTACAAAAAGGCTAAGAAGGCCAGAAAGAGAGTCGAAGATTTTTTGGAA
AAGCAAATCATCGACGTCAGAAAGGGTAAATTGCATCCAGAAGAAGGTACTGCCTT
GTACGAATTTGCTCATTGGGAAGATTTGAACGATAACCCAATGGATTCTCATTTGTG
CGCTGTTGATTTGATGAACGTTGTTAGACCATTGGCTGCCATTAACAGATTCATTTCT
TACGGTGTTAAGGTCTTGATTGAATTCGACCAAGAAAAAGAAAAGTTGAGATTGGA
AAACAACGAAGATTACGCCTACAAGTTCGCTCAAGAAGTTAGAAGAATCTTTCCATT
CGTTCCATACTTGCCAGGTAGAGCTGCAGTTGATTTGGAATATGATGGTTACAAGAT
TCCAGCTGGTATGATGACTGCTTTGGATGTTTATGGTACTACCCACGATGAAGATTT
GTGGGAAAATCCAGATCAATTCAACCCAAACAGATTCGATAATTGGGATGGTTCTCC
```

-continued

| SEQUENCES |
|---|

ATTCGATTTGATTCCACAAGGTGGTGGTGATTTCTACACTAATCATAGATGTGCTGG
TGAATGGATCACCGTTATTATCATGGAAGAAACCATGAAGTATTTCGCCAACAAGAT
CGAATTTGACGTCCCATCTCAAGATTTGTCTGTTAAGTTGGATAAGTTGCCTGGTAAT
GTTACCTCCGGTACTATTATTTCTAACGTCAGACCAAGAGTTGCCAGAAAGTAA

OleT$_{MC}$ (SEQ ID NO 2):
ATGAGAGTCGAATTCACCATCAACTACATTAACGTCGAAGGTATCTCCATGTCTAAG
AGAGTTCCAAAGGATAGAGGTATCGACAACTCCTTGAAGATTATGAAGGAAGGTTA
CGAATACGTTCCAGCCAGAATGAAGAAGTTCAACACCAACATTTTCGAAACCAGAG
TTTTGGGTGGTAAGACCGCTGTTGTTATTTCTGGTAAAGATGCTGCCGAATTATTCTA
CGATAACGACAAGACTGAAAGAAAGGGTACTTTGCCAAAGAGAGTTGTTAAGACTT
TGTTTGGTAAGGGTGCTATTCATACCACTACCGGTAAGAAACATATTGACAGAAAGG
CCTTGTTCATGTCTTTGATGACTGACGAAAATTTGGCCTACTTGAGAAAGTTGACTA
GAATCTACTGGTTCCAAAACATCGAACACATGCAATACAAGCAAAAGGTCAACGTT
TACGAAGAAGCCACTGAATTATTGACCAAGGTTGGTTTGAGATGGGCTGGTATAGTT
GATCATCCAGAAAACATTCAAAAGATGGCCGACGATATGAACAAGATGATCGATTC
TTTTTCCGCCATCGGTTCATTATATGGTGGTTACAGAGAAGCTAAAAAGGCTAGAGC
TAGAGTCGAACAATTCTTGGAAGATCAAATTACCGCTGTCAGAAAAGGTAAGATTC
ACCCAGAAAAAGGTACTGCCTTGTACGAATTTTCTCACTGGGAAGATATGAACGGTA
AACCTATGGATGCTAGATTGTGTGCTGTTGATTTGATGAACGTTATCAGACCATTGG
TTGCCATCAACAAGTTTGTTTCTTTTGGTGTTTTGGCCTTGCATGAATTTCCAGGTGA
AAGAGTTAGAGTTGCTTTGAACGAAGGTGATTACGCTTACAAGTTCGTTCAAGAAGT
CAGAAGATATTACCCATTCGTTCCATTTTTGCCAGGTAAGGCTAAAGAAAACATCAC
TTTCGATGGTTACAAGATCCAAAAGGACACCATGATGTTTGGATATCTACGGTAC
ATTGCACAGAGATGACTTGTTTTCTGAACCAGAAAGATTCAACCCATACAGATTCGA
TAATTGGGATGGTTCTCCATTCGATTTGATTCCACAAGGTGGTGGTGATTACTACACT
AATCATAGATGTGCTGGTGAATGGATGACCATCATTATTATGGAAGAAACCATGAA
GTTCTTCGCCAACGAAATCTCTTATGATGTTCCACCACAAGATTTCACTGTTGATACC
ACTAAGTTCCCAGGTAAAGTTGCTTCTGGTATGGATATCGAAAACATTAGAGTCAAC
ATCGACAGAACTAAGTAA

OleT$_{SP}$ (SEQ ID NO 3):
ATGGCTAAGAAGTTGCCAAAGGATACTGGTTTGGATAACACCTTGAAGATGATTAA
CGAAGCCTACACTTACGTCCCAAAGAGATTGGAAAAATTCGGTACTAAGGCTTTCGA
AACTAGAGCTTTGGGTATGAAGCCAATCGTTGTTATTTCTGGTAAAGCTGCTGCCGA
ATTATTCTACGATAACGACAAAATCTCCAGAAAGGGTACTTTGCCAAAGAGAATCGT
TCATACTTTGTTTGGTAAGGGTGCTATTCATACCACTGAAGGTAAAGTTCACGTTGA
TAGAAAGGCCTTGTTCATGTCTTTGATGACCGAAAAGAACTTGAAGTACTTGAGAGA
ATTGACCAGAAACTACTGGTTCATGCATACCGAAAGAATGCAAAACAAGGATGAAG
TCAACGTTTACCAAGAAGCCGGTTTGATTTTGACTAAGGTTGGTTTTAGATGGGCTG
GTTTGAAGCAAACTGATGAACAAGCTGCTCAAAACGCTGAAGATATGAACACCATG
ATCGATTCTTTTTCCGGTTTGGGTCAATCTTTGAAGGGTTACAGAGAAGCTAAAAAG
GCTAGAGCTAGAGTCGAACAATTCTTACAAGAACAAATCGAAGCCGTTAGAGTCGG
TCAACAATACGCTGAACCAGGTACTGCATTATACGAATTTGCTCATTGGAAGGACTT
GAACGATCAACCTATGGATCCACATTTGTGTGCTGTTGATTTGATGAACATCGTTAG
ACCATTGGTTGCCGTTAACAGATTTGTTTCTTATGGTGTTAAGGCCTTGATTGAATTC
GACCAAGAAAGAAAAAGTTGCAAGTTACCAACGATCCAAACTACGCTTACAAGTT
CGCTCAAGAAGTTAGAAGAATCTTCCCATTCGTTCCATTTTTGCCAGGTAGATTGAA
AAAGACCGTTGAATTTGACGGTTTCAAGTTGAAGAAGGGTACATTGACCGTTTTGGA
TATTTTCGGTACAACCCACGATCCAGAATTATTCGAAATCCATACCAATTCAACCC
AGACAGATTCGATAATTGGGATGGTTCTCCATTCGATTTGATTCCACAAGGTGGTGG
TGATTTCTACACTAATCATAGATGTGCTGGTGAATGGATGACCGTTATAGTTATGGA
AGAAACCATTCAATACTTCGCCAACAAGATCGATTTCGTTGTTCCAGCTCAAGATTT
GTCCGTTAAGTTGTCTCAATTTCCAGGTAAGGTTACCTCTGGTACTATGATCAAAAA
TGTCTACCCAAGAATTTGA

OleT$_{BS}$ (SEQ ID NO 4):
ATGAACGAACAAATCCCACACGATAAGTCCTTGGATAACTCTTTGACCTTGTTGAAA
GAAGGTTACTTGTTCATCAAGAACAGAACCGAAAGATACAACTCCGATTTGTTCCAA
GCTAGATTATTGGGTAAGAACTTCATCTGTATGACTGGTGCTGAAGCTGCTAAGGTT
TTTTACGATACTGACAGATTCCAAAGACAAAACGCTTTGCCAAAGAGAGTCCAAAA
GTCTTTGTTTGGTGTTAACGCCATTCAAGGTATGGATGGTTCTGCTCATATTCACAGA
AAGATGTTGTTCTTGTCTTTGATGACTCCACCACATCAAAAAAGATTGGCTGAATTG
ATGACCGAAGAATGGAAAGCTGCTGTTACTAGATGGGAAAAAGCTGATGAAGTTGT
CTTGTTCGAAGAAGCCAAAGAAATCTTGTGTAGAGTTGCTTGTTATTGGGCTGGTGT
TCCATTGAAAGAAACCGAAGTAAAAGAAAGAGCCGACGATTTCATCGATATGGTTG
ATGCTTTTGGTGCTGTTGGTCAAGACATTGGAAAGGTAGAAGAGCTAGACCAAGA
GCTGAAGAATGGATTGAAGTTATGATTGAAGATGCTAGAGCCGGTTTGTTGAAAACT
ACTTCTGGTACTGCTTTACACGAAATGGCTTTCCATACTCAAGAAGATGGTTCCCAA
TTGGATTCAAGAATGGCTGCTATTGAATTGATCAACGTTTTAAGACCAATCGTCGCT
ATCTCCTACTTCTTGGTTTTTTCTGCTTTGGCCTTGCATGAACACCCAAAGTACAAAG
AATGGTTGAGATCTGGTAACTCCAGAGAAAGAGAAATGTTCGTCCAAGAAGTCAGA
AGATATTACCCATTTGGTCCATTTTTGGGTGCCTTGGTTAAGAAGGATTTTGTTTGGA
CAACTGCGAATTCAAGAAGGGTACTTCTGTTTTGTTGGACTTGTACGGTACTAATC
ACGATCCAAGATTGTGGGATCATCCAGATGAATTCAGACCAGAAAGATTCGCCGAA
AGAGAAGAAACTTGTTCGACATGATTCCACAAGGTGGTGGTCATGCTGAAAAGG
TCATAGATGTCCAGGTAAGGTATTACCATTGAAGTAATGAAGGCCTCCTTGGATTT

-continued

| SEQUENCES |
|---|

TTTGGTTCACCAAATCGAATACGACGTCCCAGAACAATCATTGCATTATTCATTGGC
TAGAATGCCATCCTTGCCAGAATCTGGTTTTGTTATGTCTGGTATCAGAAGAAAGTC
TTAA

OleT$_{MP}$ (SEQ ID NO 5):
ATGCCAGCTGCTATTGCTACTCATAGATTCAGAAAAGCTAGAACCTTGCCAAGAGAA
CCAGCTCCAGATTCTACTTTGGCTTTGTTGAGAGAAGGTTACGGTTTCATTAGAAAC
AGATGCAGAAGACACGATTCCGATTTGTTTGCTGCTAGATTGTTGTTGTCTCCAGTTA
TCTGTATGTCTGGTGCTGAAGCTGCTAGACATTTTTATGATGGTCACAGATTCACCA
GAAGACATGCTTTGCCACCAACATCTTTTGCCTTGATTCAAGATCATGGTTCCGTTAT
GGTTTTGGATGGTGCTGCTCATTTGGCTAGAAAAGCAATGTTTTTGTCCTTGGTTGGT
GAAGAAGCCTTGCAAAGATTGGCTGGTTTGGCTGAAAGACATTGGAGAGAAGCTGT
TTCTGGTTGGGCAAGAAAAGATACTGTTGTTTTGTTGGATGAAGCCCACAGAGTTTT
GACTGCTGCTGTTTGTGAATGGGTTGGTTTGCCATTGGGTCCAACTGAAGTTGATGC
TAGAGCTAGAGAATTTGCTGCAATGATTGATGGTACTGGTGCTGTTGGTCCAAGAAA
TTGGAGAGGTCACTTGTATAGAGCAAGAACTGAAAGATGGGTTAGAAAGGTTATCG
ACGAAATCAGATCTGGTAGAAGAGATGTTCCACCAGGTGCTGCAAGAACTATTGCT
GAACATCAAGATGCTGACGGTCAAAGATTAGATAGAACTGTTGCTGGTGTCGAATT
GATCAACGTTTTAAGACCAACAGTTGCCAACGCCAGATATATCGTTTTCGCTGCTAT
GGCTTTACATGATCATCCACATCAAAGAGCTGCTTTAGCTGACGGTGGTGAAGCAGC
TGAAAGATTCACTGATGAAGTTAGAAGATTCTACCCATTCATCCCTTTCATTGGTGG
TAGAGTTAGAGCCCCATTTCATTTTGGTGGTCATGATTTTAGAGAAGGTGAATGGGT
CTTGATGGACTTGTATGGTACTAATAGAGATCCAAGATTGTGGCACGAACCAGAAA
GATTTGATCCAGATAGATTCGCCAGAGAAACCATTGATCCATTCAACATGGTTTCAC
ATGGTGCTGGTTCTGCTAGAGATGGTCATAGATGTCCAGGTGAAGGTATTACCAGAA
TCTTGTTGAGAACCTTGAGTAGACAATTGGCTGCTACTAGATATACAGTTCCACCAC
AAGATTTGACTTTGGATTTGGCTCATGTTCCAGCTAGACCAAGATCTGGTTTTGTTAT
GAGAGCTGTTCATGCTCCATGA

OleT$_{CE}$ (SEQ ID NO 6):
ATGGAAGAAGTTCCTCCAATGACTCAAACTTCTTCTTGTCCATTTGCTCCAGGTGAA
CAAGCTCCAAATTTGTTGAGACATGGTTACTTGTTCTTGTCTAGATTGAGAAGAAAG
GCCGGTATTTCTCCAGATGCTAATACTCCATTGAGATCCAGAATGTTGTTCAAGCCA
GTTACTATCGTTAGAGGTTCTGCTGGTGTTGAATTATTCTACGATAACGACAGAATG
AAGAGAGATGGTGCTATGCCAGCTGTTATTAGAATTCCTTTGTTTGGTGAAGGTGCC
GTTCATTCTTTGGATGGTGAAGAACATAGATTAAGAAAAAGACAATTGGCCGATGTT
GCCTACGATGATGATAAGGTTGCTGAATTTGATGCCTTGGTTAGAAGAGAAGTTGAT
AGAGTTGTACAAGATTGGGCTAGAGAACCAGGTACTGTTTATGATGGTGCTGCTTTG
GCTTTTGGTAGAGCTGCTTATAGATGGGCAGGTATTGAATTGTCTCAAAAAGAAGCT
AGTAGAAGAGCCCATCAAATGGCTGAATTGGTTTACCAATTTGGTCATCCATTGAAG
GGTCATGCTTTGGGTTGGATTAACAGAGCTAGATTGAACAGATGGGCCTTGAAGTTG
ATTAGACAAGCTAGAGCTGGTGAAAGACATGTTGCACCAGGTTCAGCTTTGGAAGC
TATGTCAAGATTGGTTGGTCCAGATGGTGAATTAGTTGATGCTTCTATTGCTGGTATC
GAATTGCAAAACTTGACTAGACCAACTGTTGCCGTTTCTTTGTTTGCTTCATTTGCTG
GTTCTGCATTGGTTGAACATCCTGAATGGGTTGAAAAGATTAGAGAAGGTGGTCAAC
CAGTTGCATTTGCTTTTGCTCAAGAAGTCAGAAGAGTTTACCCATTCGTTCCAATGTT
GCCAGCTATTGCTACTACTGATACTGAAATTCAAGGTTGCCCAGTTCATGAAGGTGA
AAGAGTTATTATCGACATCTACGGTACTAATACCGATCCAAATGAATGGGAAAATCC
ATCTGCATTCCAACCAGAAAGATTTTTGTCCAGAGAAGATTTGGGTACTCAAGAAGA
TTACGAAAGATTGACCTCTTTCGTTCCACAAGGTGGTGCTGGTGTCTATACTGGTCAT
AGATGTCCTGGTGAAAAAATTGCTATGGCTGCTTTGACTGCTATGGTTGAAGCTTTG
TGTAGACCAGGTGTTGTTTTGTCTACTGATCCAGCTGATACAAGATTTCCATGGACTC
AAATGTTGACCAGATCTGAAACTGGTATGAGAGTTAGAGTCGAAAGATAA

OleT$_{JE}$ (SEQ ID NO 7):
ATGGCAACACTTAAGAGGGATAAGGGCTTAGATAATACTTTGAAAGTATTAAAGCA
AGGTTATCTTTACACAACAAATCAGAGAAATCGTCTAAACACATCAGTTTTCCAAAC
TAAAGCACTCGGTGGTAAACCATTCGTAGTTGTGACTGGTAAGGAAGGCGCTGAAA
TGTTCTACAACAATGATGTTGTTCAACGTGAAGGCATGTTACCAAAACGTATCGTTA
ATACGCTTTTTGGTAAAGGTGCAATCCATACGGTAGATGGTAAAAAACACGTAGAC
AGAAAAGCATTGTTCATGAGCTTGATGACTGAAGGTAACTTGAATTATGTACGAGA
ATTAACGCGTACATTATGGCATGCGAACACACAACGTATGGAAAGTATGGATGAGG
TAAATATTTACCGTGAATCTATCGTACTACTTACAAAAGTAGGAACACGTTGGGCAG
GCGTTCAAGCACCACCTGAAGATATCGAAAGAATCGCAACAGACATGGACATCATG
ATCGATTCATTTAGAGCACTTGGTGGTGCCTTTAAAGGTTACAAGGCATCAAAAGAA
GCACGTCGTCGTGTTGAAGATTGGTTAGAAGAACAAATTATTGAGACTCGTAAAGG
GAATATTCATCCACCAGAAGGTACAGCACTTTACGAATTTGCACATTGGGAAGACTA
CTTAGGTAACCCAATGGACTCAAGAACTTGTGCGATTGACTTAATGAACACATTCCG
CCCATTAATCGCAATCAACAGATTCGTTTCATTCGGTTTACACGCGATGAACGAAAA
CCCAATCACACGTGAAAAAATTAAATCAGAACCTGACTATGCATATAAATTCGCTCA
AGAAGTTCGTCGTTACTATCCATTCGTTCCATTCCTTCCAGGTAAAGCGAAAGTAGA
CATCGACTTCCAAGGCGTTACAATTCCTGCAGGTGTAGGTCTTGCATTAGATGTTTAT
GGTACAACGCATGATGAATCACTTTGGGACGATCCAAATGAATTCCGCCCAGAAAG
ATTCGAAACTTGGGACGGATCACCATTTGACCTTATTCCACAAGGTGGTGGAGATTA

| SEQUENCES |
|---|
| CTGGACAAATCACCGTTGTGCAGGTGAATGGATCACAGTAATCATCATGGAAGAAA<br>CAATGAAATACTTTGCAGAAAAAATAACTTATGATGTTCCAGAACAAGATTTAGAA<br>GTGGACTTAAACAGTATCCCAGGATACGTTAAGAGTGGCTTTGTAATCAAAAATGTT<br>CGCGAAGTTGTAGACAGAACATAA<br><br>OleT$_{JE\text{-}CO}$ (SEQ ID NO 8):<br>ATGGCTACTTTGAAGAGAGATAAGGGTTTGGATAACACCTTGAAGGTTTTGAAGCA<br>AGGTTACTTGTACACCACCAATCAAAGAAACAGATTGAACACCTCCGTTTTCCAAAC<br>AAAAGCTTTGGGTGGTAAGCCATTCGTTGTTGTTACTGGTAAAGAAGGTGCTGAAAT<br>GTTCTACAACAATGACGTTGTTCAAAGAGAAGGTATGTTGCCAAAGAGAATTGTCA<br>ACACTTTGTTTGGTAAGGGTGCCATTCATACTGTTGATGGTAAGAAACACGTTGACA<br>GAAAGGCTTTGTTCATGTCTTTGATGACTGAAGGTAACTTGAACTACGTCAGAGAAT<br>TGACTAGAACTTTGTGGCATGCTAACACCCAAAGAATGGAATCTATGGATGAAGTC<br>AACATCTACAGAGAATCCATCGTTTTGTTGACCAAGGTTGGTACTAGATGGGCTGGT<br>GTTCAAGCTCCACCAGAAGATATTGAAAGAATTGCTACCGATATGGACATCATGATC<br>GATTCTTTTAGAGCTTTAGGTGGTGCTTTCAAAGGTTACAAGGCTTCTAAAGAAGCC<br>AGAAGAAGAGTTGAAGATTGGTTGGAAGAACAAATCATCGAAACCAGAAAGGGTA<br>ACATTCATCCACCTGAAGGTACTGCCTTGTATGAATTTGCTCATTGGGAAGATTACTT<br>GGGTAACCCAATGGATTCTAGAACCTGTGCTATTGATTTGATGAACACCTTCAGACC<br>ATTGATCGCCATTAACAGATTTGTTTCTTTCGGTTTACACGCCATGAACGAAAACCC<br>AATTACCAGAGAAAAGATCAAGTCCGAACCAGATTACGCTTACAAGTTTGCTCAAG<br>AAGTTAGAAGATATTACCCATTCGTCCCATTTTTGCCAGGTAAAGCTAAGGTTGATA<br>TCGATTTCCAAGGTGTCACTATTCCAGCTGGTGTTGGTTTGGCTTTGGATGTTTATGG<br>TACTACCCATGATGAATCCTTGTGGGATGATCCAAATGAATTCAGACCAGAAAGATT<br>CGAAACTTGGGATGGTTCTCCATTCGATTTGATTCCACAAGGTGGTGGTGATTACTG<br>GACTAATCATAGATGTGCCGGTGAATGGATTACCGTTATTATCATGGAAGAAACCAT<br>GAAGTACTTTGCCGAAAAGATTACCTACGATGTTCCAGAACAAGATTTGGAAGTTGA<br>CTTGAACTCTATTCCAGGTTACGTTAAGTCCGGTTTCGTTATTAAGAACGTTAGAGA<br>AGTTGTCGACAGAACTTAA |

---

What is claimed is:

1. A modified *Saccharomyces cerevisiae* yeast wherein the modification comprises:
   insertion of at least one heterologous fatty acid decarboxylase gene encoding a fatty acid decarboxylase that synthesizes terminal alkenes selected from 1-undecene, 1-tridecene, 1-pentadecene, 1-heptadecene or 1-nonadecene,
   deletion of fatty acyl-Coenzyme A synthetases, FAA1 and FAA4,
   overexpression of porphobilinogen deaminase, HEM3, and
   triple-deletion of catalase T, CTT1, catalase A CTA1 and cytochrome c peroxidase, CCP1.

2. The modified *Saccharomyces cerevisiae* yeast of claim 1, wherein the yeast produces at least one terminal alkene.

3. The modified *Saccharomyces cerevisiae* yeast of claim 1, wherein the fatty acid decarboxylase is selected for terminal alkene synthesis via a one-step fatty acid decarboxylation pathway.

4. The modified *Saccharomyces cerevisiae* yeast of claim 3, wherein the fatty acid decarboxylase is $OleT_{SM}$ (SEQ ID NO 1), $OleT_{MC}$ (SEQ ID NO 2), $OleT_{SP}$ (SEQ ID NO 3), $OleT_{BS}$ (SEQ ID NO 4), $OleT_{CE}$ (SEQ ID NO 6), $OleT_{JE}$ (SEQ ID NO 7) or $OleT_{JE\text{-}CO}$ (SEQ ID NO 8).

5. The modified *Saccharomyces cerevisiae* yeast of claim 1, characterized by BY22 (BY4741, Δfaa1 Δfaa4 Δctt1 Δcta1 Δccp1, $P_{TEF1}$-HEM3 with pRS41K-$P_{TEF1}$-$OleT_{JE\text{-}CO}$).

6. A method of producing at least one terminal alkene, the method comprising:

culturing the modified *Saccharomyces cerevisiae* yeast of claim 1 in a rich growth medium;

fermenting the culture of modified *Saccharomyces cerevisiae* yeast at a temperature of about 25° C. to about 35° C. under aerobic conditions to produce at least one terminal alkene, wherein the terminal alkene is 1-undecene, 1-tridecene, 1-pentadecene, 1-heptadecene or 1-nonadecene; and harvesting the at least one terminal alkene, wherein the harvesting comprises lysing the yeast cells and extracting the terminal alkene.

7. The method of claim 6, wherein the rich growth medium is selected from SC-U+GAL, YPG+G418, YPD+G418 or YPD.

8. The method of claim 6, wherein the fermenting is performed with a dissolved oxygen concentration of about 60%.

9. The method of claim 6, wherein the fermenting is performed at a temperature of about 30° C.

10. The method of claim 6, wherein the fermenting is performed without pH control.

* * * * *

SEQUENCE LISTING

<160> NUMBER OF SEQ ID NOS: 32

<210> SEQ ID NO 1
<211> LENGTH: 1362
<212> TYPE: DNA
<213> ORGANISM: Staphylococcus massiliensis

<400> SEQUENCE: 1

```
atgttcgtcg attccatctt ggtcttgaga ttgaacttgt tgaaaaccgg tatacaattg      60
gaaatgaaga acgtggtat taaggttgct aagaaattgc caaaggttaa gggtttggat     120
aacaccgttg atatcattaa gggtggttac acttacgttc aggtaagtt ggaagaattc     180 gattctaagg ctttcgaagt tagagctttg ggtggtaaaa agattgctgt catgtctggt     240
aaagaagccg ctgaaatttt ctacgacaac gaaaagatgg aaagacaagg tactttgcca     300
aagagaatcg ttaacacttt gtttggtaag ggtgctattc ataccactgc tggtaaaaaa     360
cacgttgata gaaaggcctt gttcatgtct ttgatgactg acgaaaactt gaactacttg     420
agagaattga ccagaaacta ctggtttatg aacaccgaaa gaatgcaatc catggacaag     480
gttaacgtct acaacgaatc tatctacatg ttgaccaaga tcggttttag atgggccggt     540
attattcaaa ctcctgaaga agctgaacaa aacgctaaag atatggacac catgatcaac     600
tcattcgtca gtttgggttc tgcttacaaa ggttacaaaa aggctaagaa ggccagaaag     660
agagtcgaag atttttttgga aaagcaaatc atcgacgtca gaagggtaa attgcatcca     720 gaagaaggta ctgccttgta cgaatttgct cattgggaag atttgaacga taacccaatg     780
gattctcatt tgtgcgctgt tgatttgatg aacgttgtta gaccattggc tgccattaac     840
agattcattt cttacggtgt taaggtcttg attgaattcg accaagaaaa agaaaagttg     900
agattggaaa acaacgaaga ttacgcctac aagttcgctc aagaagttag aagaatcttt     960
```

```
ccattcgttc catacttgcc aggtagagct gcagttgatt tggaatatga tggttacaag    1020
attccagctg gtatgatgac tgctttggat gtttatggta ctacccacga tgaagatttg    1080
tgggaaaatc cagatcaatt caacccaaac agattcgata attgggatgg ttctccattc    1140
gatttgattc cacaaggtgg tggtgatttc tacactaatc atagatgtgc tggtgaatgg    1200
atcaccgtta ttatcatgga agaaaccatg aagtatttcg ccaacaagat cgaatttgac    1260
gtcccatctc aagatttgtc tgttaagttg gataagttgc tggtaatgtt acctccggt    1320 actattattt ctaacgtcag accaagagtt gccagaaagt aa                      1362

<210> SEQ ID NO 2
<211> LENGTH: 1326
<212> TYPE: DNA
<213> ORGANISM: Macrococcus caseolyticus JCSC5402

<400> SEQUENCE: 2
atgagagtcg aattcaccat caactacatt aacgtcgaag gtatctccat gtctaagaga      60
gttccaaagg atagaggtat cgacaactcc ttgaagatta tgaaggaagg ttacgaatac    120
gttccagcca gaatgaagaa gttcaacacc aacattttcg aaaccagagt tttgggtggt    180
aagaccgctg ttgttatttc tggtaaagat gctgccgaat tattctacga taacgacaag    240
actgaaagaa agggtacttt gccaaagaga gttgttaaga ctttgtttgg taagggtgct    300
attcatacca ctaccggtaa gaaacatatt gacagaaagg ccttgttcat gtctttgatg    360
actgacgaaa atttggccta cttgagaaag ttgactagaa tctactggtt ccaaaacatc    420
gaacacatgc aatacaagca aaaggtcaac gtttacgaag aagccactga attattgacc    480
aaggttggtt tgagatgggc tggtatagtt gatcatccag aaaacattca aaagatggcc    540
gacgatatga acaagatgat cgattctttt tccgccatcg gttcattata tggtggttac    600
agagaagcta aaaaggctag agctagagtc gaacaattct tggaagatca aattaccgct    660
gtcagaaaag gtaagattca cccagaaaaa ggtactgcct tgtacgaatt ttctcactgg    720
gaagatatga acggtaaacc tatggatgct agattgtgtg ctgttgattt tgatgaacgtt    780 atcagaccat tggttgccat caacaagttt gtttcttttg tgttttggc cttgcatgaa    840 tttccaggtg aaagagttag agttgctttg aacgaaggtg attacgctta caagttcgtt    900
caagaagtca aagatatta cccattcgtt ccattttgc aggtaaggc taagaaaaac    960 atcactttcg atggttacaa gatccaaaag gacaccatga tgttgttgga tatctacggt    1020
acattgcaca gagatgactt gttttctgaa ccagaaagat tcaacccata cagattcgat    1080
aattgggatg gttctccatt cgatttgatt ccacaaggtg gtggtgatta ctacactaat    1140
catagatgtg ctggtgaatg gatgaccatc attattatgg aagaaaccat gaagttcttc    1200
gccaacgaaa tctcttatga tgttccacca caagatttca ctgttgatac cactaagttc    1260
ccaggtaaag ttgcttctgg tatggatatc gaaaacatta gagtcaacat cgacagaact    1320
aagtaa                                                                1326

<210> SEQ ID NO 3
<211> LENGTH: 1269
<212> TYPE: DNA
<213> ORGANISM: Staphylococcus pseudintermedius ED99

<400> SEQUENCE: 3
atggctaaga agttgccaaa ggatactggt ttggataaca ccttgaagat gattaacgaa      60
gcctacactt acgtcccaaa gagattggaa aaattcggta ctaaggcttt cgaaactaga    120
```

```
gctttgggta tgaagccaat cgttgttatt tctggtaaag ctgctgccga attattctac      180
gataacgaca aaatctccag aaagggtact ttgccaaaga gaatcgttca tactttgttt      240
ggtaagggtg ctattcatac cactgaaggt aaagttcacg ttgatagaaa ggccttgttc      300
atgtctttga tgaccgaaaa gaacttgaag tacttgagag aattgaccag aaactactgg      360
ttcatgcata ccgaaagaat gcaaaacaag gatgaagtca acgtttacca gaagccggt       420 ttgattttga ctaaggttgg ttttagatgg gctggtttga agcaaactga tgaacaagct      480
gctcaaaacg ctgaagatat gaacaccatg atcgattctt tttccggttt gggtcaatct      540
ttgaagggtt acagagaagc taaaaaggct agagctagat cgaacaatt cttacaagaa       600 caaatcgaag ccgttagagt cggtcaacaa tacgctgaac caggtactgc attatacgaa      660
tttgctcatt ggaaggactt gaacgatcaa cctatggatc cacatttgtg tgctgttgat      720
ttgatgaaca tcgttagacc attggttgcc gttaacagat ttgtttctta tggtgttaag      780
gccttgattg aattcgacca agaaagaaaa aagttgcaag ttaccaacga tccaaactac      840
gcttacaagt tcgctcaaga agttagaaga atcttcccat tcgttccatt tttgccaggt      900
agattgaaaa agaccgttga atttgacggt ttcaagttga agaagggtac attgaccgtt      960
ttggatattt tcggtacaac ccacgatcca gaattattcg aaaatccata ccaattcaac     1020
ccagacagat tcgataattg ggatggttct ccattcgatt tgattccaca aggtggtggt     1080
gatttctaca ctaatcatag atgtgctggt gaatggatga ccgttatagt tatggaagaa     1140
accattcaat acttcgccaa caagatcgat ttcgttgttc cagctcaaga tttgtccgtt     1200
aagttgtctc aatttccagg taaggttacc tctggtacta tgatcaaaaa tgtctaccca     1260
agaatttga                                                             1269

<210> SEQ ID NO 4
<211> LENGTH: 1254
<212> TYPE: DNA
<213> ORGANISM: Bacillus subtilis 168

<400> SEQUENCE: 4
atgaacgaac aaatcccaca cgataagtcc ttggataact ctttgacctt gttgaaagaa       60
ggttacttgt tcatcaagaa cagaaccgaa agatacaact ccgatttgtt ccaagctaga     120
ttattgggta agaacttcat ctgtatgact ggtgctgaag ctgctaaggt tttttacgat     180
actgacagat tccaaagaca aaacgctttg ccaagagagt ccaaaagtc tttgtttggt      240 gttaacgcca ttcaaggtat ggatggttct gctcatattc acagaaagat gttgttcttg     300 tcttttgatga ctccaccaca tcaaaaaaga ttggctgaat tgatgaccga gaatggaaa    360 gctgctgtta ctagatggga aaaagctgat gaagttgtct tgttcgaaga agccaaagaa     420
atcttgtgta gagttgcttg ttattgggct ggtgttccat gaaagaaac cgaagtaaaa     480 gaaagagccg acgatttcat cgatatggtt gatgcttttg gtgctgttgg tccaagacat     540 tggaaggta gaagagctag accaagagct gaagaatgga ttgaagttat gattgaagat     600
gctagagccg gtttgttgaa aactacttct ggtactgctt acacgaaat ggctttccat     660 actcaagaag atggttccca attggattca agaatggctg ctattgaatt gatcaacgtt     720
ttaagaccaa tcgtcgctat ctcctacttc ttggtttttt ctgctttggc cttgcatgaa     780
cacccaaagt acaagaatg gttgagatct ggtaactcca gagaaagaga atgttcgtc     840 caagaagtca gaagatatta cccatttggt ccatttttgg gtgccttggt taagaaggat     900
```

```
tttgtttgga caaactgcga attcaagaag ggtacttctg ttttgttgga cttgtacggt   960
actaatcacg atccaagatt gtgggatcat ccagatgaat tcagaccaga aagattcgcc  1020
gaaagagaag aaaacttgtt cgacatgatt ccacaaggtg gtggtcatgc tgaaaaaggt  1080
catagatgtc caggtgaagg tattaccatt gaagtaatga aggcctcctt ggatttttg   1140
gttcaccaaa tcgaatacga cgtcccagaa caatcattgc attattcatt ggctagaatg  1200
ccatccttgc cagaatctgg tttgttatg tctggtatca gaagaaagtc ttaa         1254
```

<210> SEQ ID NO 5
<211> LENGTH: 1275
<212> TYPE: DNA
<213> ORGANISM: Methylobacterium populi BJ001

<400> SEQUENCE: 5

```
atgccagctg ctattgctac tcatagattc agaaaagcta gaaccttgcc aagagaacca    60
gctccagatt ctactttggc tttgttgaga gaaggttacg gtttcattag aaacagatgc   120
agaagacacg attccgattt gtttgctgct agattgttgt tgtctccagt tatctgtatg   180
tctggtgctg aagctgctag acattttat gatggtcaca gattcaccag aagacatgct    240
ttgccaccaa catcttttgc cttgattcaa gatcatggtt ccgttatggt tttggatggt   300
gctgctcatt tggctagaaa agcaatgttt tgtccttgg ttggtgaaga agccttgcaa    360
agattggctg gtttggctga agacattgg agagaagctg tttctggttg ggcaagaaaa   420
gatactgttg tttttgttgga tgaagcccac agagttttga ctgctgctgt tgtgaatgg   480
gttggtttgc cattgggtcc aactgaagtt gatgctagag ctagagaatt tgctgcaatg   540
attgatggta ctggtgctgt tggtccaaga aattggagag gtcacttgta tagagcaaga   600
actgaaagat gggttagaaa ggttatcgac gaaatcagat ctggtagaag agatgttcca   660
ccaggtgctg caagaactat tgctgaacat caagatgctg acggtcaaag attagataga   720
actgttgctg gtgtcgaatt gatcaacgtt ttaagaccaa cagttgccaa cgccagatat   780
atcgttttcg ctgctatggc tttacatgat catccacatc aaagagctgc tttagctgac   840
ggtggtgaag cagctgaaag attcactgat gaagttagaa gattctaccc attcatccct   900
ttcattggtg gtagagttag agccccattt cattttggtg gtcatgattt tagagaaggt   960
gaatgggtct tgatggactt gtatggtact aatagagatc caagattgtg gcacgaacca  1020
gaaagatttg atccagatag attcgccaga gaaaccattg atccattcaa catggttca   1080
catggtgctg gttctgctag agatggtcat agatgtccag gtgaaggtat taccagaatc  1140
ttgttgagaa ccttgagtag acaattggct gctactagat atacagttcc accacaagat  1200
ttgactttgg atttggctca tgttccagct agaccaagat ctggttttgt tatgagagct  1260
gttcatgctc catga                                                   1275
```

<210> SEQ ID NO 6
<211> LENGTH: 1308
<212> TYPE: DNA
<213> ORGANISM: Corynebacterium efficiens YS-314

<400> SEQUENCE: 6

```
atggaagaag ttcctccaat gactcaaact tcttcttgtc catttgctcc aggtgaacaa    60
gctccaaatt tgttgagaca tggttacttg ttcttgtcta gattgagaag aaaggccggt   120
atttctccag atgctaatac tccattgaga tccagaatgt tgttcaagcc agttactatc   180
gttagaggtt ctgctggtgt tgaattattc tacgataacg acagaatgaa gagagatggt   240
```

```
gctatgccag ctgttattag aattcctttg tttggtgaag gtgccgttca ttctttggat    300
ggtgaagaac atagattaag aaaaagacaa ttggccgatg ttgcctacga tgatgataag    360
gttgctgaat tgatgccttt ggttagaaga gaagttgata gagttgtaca agattgggct    420
agagaaccag gtactgttta tgatggtgct gctttggctt ttggtagagc tgcttataga    480
tgggcaggta ttgaattgtc tcaaaaagaa gctagtagaa gagcccatca aatggctgaa    540
ttggtttacc aatttggtca tccattgaag ggtcatgctt tgggttggat taacagagct    600
agattgaaca gatgggcctt gaagttgatt agacaagcta gagctggtga agacatgtt     660 gcaccaggtt cagctttgga agctatgtca agattggttg gtccagatgg tgaattagtt    720
gatgcttcta ttgctggtat cgaattgcaa aacttgacta gaccaactgt tgccgtttct    780
ttgtttgctt catttgctgg ttctgcattg gttgaacatc ctgaatgggt tgaaaagatt    840
agagaaggtg gtcaaccagt tgcatttgct tttgctcaag aagtcagaag agtttaccca    900
ttcgttccaa tgttgccagc tattgctact actgatactg aaattcaagg ttgcccagtt    960
catgaaggtg aaagagttat tatcgacatc tacggtacta ataccgatcc aaatgaatgg    1020
gaaaatccat ctgcattcca accagaaaga tttttgtcca gagaagattt gggtactcaa    1080
gaagattacg aaagattgac ctctttcgtt ccacaaggtg gtgctggtgt ctatactggt    1140
catagatgtc ctggtgaaaa aattgctatg gctgctttga ctgctatggt tgaagctttg    1200
tgtagaccag gtgttgtttt gtctactgat ccagctgata caagatttcc atggactcaa    1260
atgttgacca gatctgaaac tggtatgaga gttagagtcg aaagataa               1308
```

<210> SEQ ID NO 7
<211> LENGTH: 1269
<212> TYPE: DNA
<213> ORGANISM: Jeotgalicoccus sp. ATCC 8456

<400> SEQUENCE: 7

```
atggcaacac ttaagaggga taagggctta gataatactt tgaaagtatt aaagcaaggt    60
tatctttaca caacaaatca gagaaatcgt ctaaacacat cagttttcca aactaaagca    120
ctcggtggta aaccattcgt agttgtgact ggtaaggaag gcgctgaaat gttctacaac    180
aatgatgttg ttcaacgtga aggcatgtta ccaaaacgta tcgttaatac gcttttggt    240 aaaggtgcaa tccatacggt agatggtaaa aaacacgtag acagaaaagc attgttcatg    300
agcttgatga ctgaaggtaa cttgaattat gtacgagaat taacgcgtac attatggcat    360
gcgaacacac aacgtatgga aagtatggat gaggtaaata tttaccgtga atctatcgta    420
ctacttacaa agtaggaac acgttgggca ggcgttcaag caccacctga agatatcgaa    480
agaatcgcaa cagacatgga catcatgatc gattcattta gagcacttgg tggtgccttt    540
aaaggttaca aggcatcaaa agaagcacgt cgtcgtgttg aagattggtt agaagaacaa    600
attattgaga ctcgtaaagg gaatattcat ccaccagaag gtacagcact ttacgaattt    660
gcacattggg aagactactt aggtaaccca atggactcaa gaacttgtgc gattgactta    720
atgaacacat ccgcccatt aatcgcaatc aacagattcg tttcattcgg tttacacgcg    780
atgaacgaaa acccaatcac acgtgaaaaa attaaatcag aacctgacta tgcatataaa    840
ttcgctcaag aagttcgtcg ttactatcca ttcgttccat tccttccagg taaagcgaaa    900
gtagacatcg acttccaagg cgttacaatt cctgcaggtg taggtcttgc attagatgtt    960
tatggtacaa cgcatgatga atcactttgg gacgatccaa atgaattccg cccagaaaga    1020
```

```
ttcgaaactt gggacggatc accatttgac cttattccac aaggtggtgg agattactgg    1080
acaaatcacc gttgtgcagg tgaatggatc acagtaatca tcatggaaga aacaatgaaa    1140
tactttgcag aaaaaataac ttatgatgtt ccagaacaag atttagaagt ggacttaaac    1200
agtatcccag gatacgttaa gagtggcttt gtaatcaaaa atgttcgcga agttgtagac    1260
agaacataa                                                             1269

<210> SEQ ID NO 8
<211> LENGTH: 1269
<212> TYPE: DNA
<213> ORGANISM: Jeotgalicoccus sp. ATCC 8456

<400> SEQUENCE: 8
atggctactt tgaagagaga taagggtttg gataacacct tgaaggtttt gaagcaaggt      60
tacttgtaca ccaccaatca agaaacaga ttgaaccct ccgttttcca aacaaaagct      120
ttgggtggta agccattcgt tgttgttact ggtaaagaag gtgctgaaat gttctacaac     180
aatgacgttg tcaaagaga aggtatgttg ccaaagagaa ttgtcaacac tttgtttggt     240
aagggtgcca ttcatactgt tgatggtaag aaacacgttg acagaaaggc tttgttcatg    300
tctttgatga ctgaaggtaa cttgaactac gtcagagaat tgactagaac tttgtggcat    360
gctaacaccc aaagaatgga atctatggat gaagtcaaca tctacagaga atccatcgtt    420
ttgttgacca aggttggtac tagatgggct ggtgttcaag ctccaccaga agatattgaa    480
agaattgcta ccgatatgga catcatgatc gattcttta gagctttagg tggtgctttc    540
aaaggttaca aggcttctaa agaagccaga agaagagttg aagattggtt ggaagaacaa    600
atcatcgaaa ccagaaaggg taacattcat ccacctgaag gtactgcctt gtatgaattt    660
gctcattggg aagattactt gggtaaccca atggattcta gaacctgtgc tattgatttg    720
atgaacacct tcagaccatt gatcgccatt aacagatttg tttctttcgg tttacacgcc    780
atgaacgaaa acccaattac cagagaaaag atcaagtccg aaccagatta cgcttacaag    840
tttgctcaag aagttagaag atattccca ttcgtcccat ttttgccagg taaagctaag    900
gttgatatcg atttccaagg tgtcactatt ccagctggtg ttggttggc tttggatgtt    960 tatggtacta cccatgatga atccttgtgg gatgatccaa atgaattcag accagaaaga    1020
ttcgaaactt gggatggttc tccattcgat ttgattccac aaggtggtgg tgattactgg    1080
actaatcata gatgtgccgg tgaatggatt accgttatta tcatggaaga aaccatgaag    1140
tactttgccg aaaagattac ctacgatgtt ccagaacaag atttgaagt tgacttgaac    1200 tctattccag gttacgttaa gtccggtttc gttattaaga acgttagaga agttgtcgac    1260
agaacttaa                                                             1269

<210> SEQ ID NO 9
<211> LENGTH: 47
<212> TYPE: DNA
<213> ORGANISM: Artificial Sequence
<220> FEATURE:
<223> OTHER INFORMATION: Primer

<400> SEQUENCE: 9
acgcggatcc taaaaaatgt ctacacttaa gagggataag ggcttag                   47

<210> SEQ ID NO 10
<211> LENGTH: 61
<212> TYPE: DNA
<213> ORGANISM: Artificial Sequence
```

<220> FEATURE:
<223> OTHER INFORMATION: Primer

<400> SEQUENCE: 10
ataagaatgc ggccgcctaa tggtgatggt gatgatgtgt tctgtctaca acttcgcgaa    60
c    61

<210> SEQ ID NO 11
<211> LENGTH: 90
<212> TYPE: DNA
<213> ORGANISM: Artificial Sequence
<220> FEATURE:
<223> OTHER INFORMATION: Primer

<400> SEQUENCE: 11 agaattttg aaaattcgaa ttcaaccctc actaagggc ggccgcacta gttaaaaat    60 gtctgaagaa agcttattcg agtcttctcc    90

<210> SEQ ID NO 12
<211> LENGTH: 95
<212> TYPE: DNA
<213> ORGANISM: Artificial Sequence
<220> FEATURE:
<223> OTHER INFORMATION: Primer

<400> SEQUENCE: 12
taagagctca gatcttatcg tcgtcatcct tgtaatccat cgatactagt ctaatggtga    60
tggtgatgat gtttcaaagt cttcaacaat ttttc    95

<210> SEQ ID NO 13
<211> LENGTH: 64
<212> TYPE: DNA
<213> ORGANISM: Artificial Sequence
<220> FEATURE:
<223> OTHER INFORMATION: Primer

<400> SEQUENCE: 13
caataaaaac tagaacaaac acaaagaca aaaaagaca acaatcagct gaagcttcgt    60
acgc    64

<210> SEQ ID NO 14
<211> LENGTH: 67
<212> TYPE: DNA
<213> ORGANISM: Artificial Sequence
<220> FEATURE:
<223> OTHER INFORMATION: Primer

<400> SEQUENCE: 14
tgctttagta tgatgaggct ttcctatcat ggaaatgttg atccagcata ggccactagt    60
ggatctg    67

<210> SEQ ID NO 15
<211> LENGTH: 64
<212> TYPE: DNA
<213> ORGANISM: Artificial Sequence
<220> FEATURE:
<223> OTHER INFORMATION: Primer

<400> SEQUENCE: 15
tctgttcttc actatttctt gaaaaactaa gaagtacgca tcaaacagct gaagcttcgt    60
acgc    64

<210> SEQ ID NO 16
<211> LENGTH: 67
<212> TYPE: DNA
<213> ORGANISM: Artificial Sequence
<220> FEATURE:
<223> OTHER INFORMATION: Primer

<400> SEQUENCE: 16
gtgtttatga agggcagggg ggaaagtaaa aaactatgtc ttcctgcata ggccactagt    60
ggatctg                                                              67

<210> SEQ ID NO 17
<211> LENGTH: 42
<212> TYPE: DNA
<213> ORGANISM: Artificial Sequence
<220> FEATURE:
<223> OTHER INFORMATION: Primer

<400> SEQUENCE: 17
ttgagagctc tttcatagct tcaaaatgtt tctactcctt tt                        42

<210> SEQ ID NO 18
<211> LENGTH: 48
<212> TYPE: DNA
<213> ORGANISM: Artificial Sequence
<220> FEATURE:
<223> OTHER INFORMATION: Primer

<400> SEQUENCE: 18
tcagggccca ttttgtaatt aaaacttaga ttagattgct atgctttc                  48

<210> SEQ ID NO 19
<211> LENGTH: 48
<212> TYPE: DNA
<213> ORGANISM: Artificial Sequence
<220> FEATURE:
<223> OTHER INFORMATION: Primer

<400> SEQUENCE: 19
ctaatctaag ttttaattac aaaatgggcc ctgaaactct acatattg                  48

<210> SEQ ID NO 20
<211> LENGTH: 60
<212> TYPE: DNA
<213> ORGANISM: Artificial Sequence
<220> FEATURE:
<223> OTHER INFORMATION: Primer

<400> SEQUENCE: 20
cttatttagt caatggtgat ggtgatgatg tttgattctg tctaaattaa tttcatccag    60

<210> SEQ ID NO 21
<211> LENGTH: 56
<212> TYPE: DNA
<213> ORGANISM: Artificial Sequence
<220> FEATURE:
<223> OTHER INFORMATION: Primer

<400> SEQUENCE: 21
catcatcacc atcaccattg actaaataag cgaatttctt atgatttatg attttt        56

<210> SEQ ID NO 22
<211> LENGTH: 32
<212> TYPE: DNA
<213> ORGANISM: Artificial Sequence

```
<220> FEATURE:
<223> OTHER INFORMATION: Primer

<400> SEQUENCE: 22
acggggtacc tttcagctga attggagcga cc                                   32

<210> SEQ ID NO 23
<211> LENGTH: 64
<212> TYPE: DNA
<213> ORGANISM: Artificial Sequence
<220> FEATURE:
<223> OTHER INFORMATION: Primer

<400> SEQUENCE: 23
ttctcttgtc tcatgccaat aagatcaatc agctcagctt cacaacagct gaagcttcgt     60
acgc                                                                  64

<210> SEQ ID NO 24
<211> LENGTH: 67
<212> TYPE: DNA
<213> ORGANISM: Artificial Sequence
<220> FEATURE:
<223> OTHER INFORMATION: Primer

<400> SEQUENCE: 24
ttatggagat ataattacga ataattatga ataaatagtg ctgccgcata ggccactagt     60
ggatctg                                                               67

<210> SEQ ID NO 25
<211> LENGTH: 64
<212> TYPE: DNA
<213> ORGANISM: Artificial Sequence
<220> FEATURE:
<223> OTHER INFORMATION: Primer

<400> SEQUENCE: 25
aaataaatat aatagtactt acaaataaat ttggaaccct agaagcagct gaagcttcgt     60
acgc                                                                  64

<210> SEQ ID NO 26
<211> LENGTH: 67
<212> TYPE: DNA
<213> ORGANISM: Artificial Sequence
<220> FEATURE:
<223> OTHER INFORMATION: Primer

<400> SEQUENCE: 26
ataattgtcg tggaaacaac gccactcatt tgttacttga gcgttgcata ggccactagt     60
ggatctg                                                               67

<210> SEQ ID NO 27
<211> LENGTH: 64
<212> TYPE: DNA
<213> ORGANISM: Artificial Sequence
<220> FEATURE:
<223> OTHER INFORMATION: Primer

<400> SEQUENCE: 27
atttcgcatt catgcagacg caaacacaca cgtatatcta caattcagct gaagcttcgt     60
acgc                                                                  64

<210> SEQ ID NO 28
```

```
<211> LENGTH: 67
<212> TYPE: DNA
<213> ORGANISM: Artificial Sequence
<220> FEATURE:
<223> OTHER INFORMATION: Primer

<400> SEQUENCE: 28
aataatacga aatataacca ataaataata tctttcctca gtgacgcata ggccactagt      60
ggatctg                                                               67

<210> SEQ ID NO 29
<211> LENGTH: 40
<212> TYPE: DNA
<213> ORGANISM: Artificial Sequence
<220> FEATURE:
<223> OTHER INFORMATION: Primer

<400> SEQUENCE: 29
ataagaatgc ggccgctaac aaaaatcacg atctgggtgg                           40

<210> SEQ ID NO 30
<211> LENGTH: 48
<212> TYPE: DNA
<213> ORGANISM: Artificial Sequence
<220> FEATURE:
<223> OTHER INFORMATION: Primer

<400> SEQUENCE: 30
ttatctctct tcaaagtagc cattttaggc tggtatcttg attctaaa                  48

<210> SEQ ID NO 31
<211> LENGTH: 49
<212> TYPE: DNA
<213> ORGANISM: Artificial Sequence
<220> FEATURE:
<223> OTHER INFORMATION: Primer

<400> SEQUENCE: 31
aactcatcat caccatcacc attaataaga tccgctctaa ccgaaaagg                 49

<210> SEQ ID NO 32
<211> LENGTH: 30
<212> TYPE: DNA
<213> ORGANISM: Artificial Sequence
<220> FEATURE:
<223> OTHER INFORMATION: Primer

<400> SEQUENCE: 32
aaacgagctc cttcgagcgt cccaaaacct                                      30
```